United States Patent [19]
Shepard et al.

[11] Patent Number: 4,788,192
[45] Date of Patent: Nov. 29, 1988

[54] 2-SULFAMOYLBENZO(B)THIOPHENE DERIVATIVES PHARMACEUTICAL COMPOSITIONS AND USE

[75] Inventors: Kenneth L. Shepard, North Wales; Samuel L. Graham, Lansdale, both of Pa.

[73] Assignee: Merck & Co., Inc., Rahway, N.J.

[21] Appl. No.: 25,242

[22] Filed: Mar. 12, 1987

Related U.S. Application Data

[60] Division of Ser. No. 600,695, Apr. 16, 1984, Pat. No. 4,668,697, which is a continuation-in-part of Ser. No. 547,191, Oct. 31, 1983, abandoned, which is a continuation-in-part of Ser. No. 506,092, Jun. 20, 1983, abandoned.

[51] Int. Cl.$^4$ .................. A61K 31/38; A61K 31/535; C07D 333/62; C07D 413/02
[52] U.S. Cl. ...................... 514/233.5; 514/254; 514/324; 514/422; 514/443; 544/145; 544/376; 546/202; 549/54; 549/55
[58] Field of Search ............ 549/52, 54, 60, 61, 549/55; 548/347, 354, 527, 274, 525; 546/184, 284, 347, 202; 544/146, 327, 379, 145, 376; 514/227, 238, 255, 276, 315, 326, 351, 396, 401, 408, 444, 233.5, 254, 324, 422, 443

[56] References Cited

U.S. PATENT DOCUMENTS

| 3,428,655 | 2/1969 | Melton et al. | 549/57 |
| 3,639,613 | 2/1972 | Dunn et al. | 549/63 |
| 4,298,613 | 5/1980 | Lepone | 549/55 |
| 4,386,098 | 5/1983 | Woltersdorf, Jr. | 424/270 |
| 4,426,388 | 1/1984 | Woltersdorf, Jr. | 548/166 |
| 4,472,417 | 9/1984 | Woltersdorf, Jr. | 546/198 |
| 4,472,418 | 9/1984 | Woltersdorf, Jr. | 546/198 |
| 4,477,466 | 10/1984 | Shepard | 546/208 |
| 4,500,538 | 2/1985 | Woltersdorf | 514/367 |
| 4,619,939 | 10/1986 | Maren | 514/363 |

FOREIGN PATENT DOCUMENTS

| 0508983 | 1/1955 | Canada | 548/167 |
| 1459571 | 12/1976 | United Kingdom | 549/55 |
| 2081712 | 2/1982 | United Kingdom | 549/55 |

Primary Examiner—Robert W. Ramsuer
Attorney, Agent, or Firm—William H. Nicholson; Michael C. Sudol

[57] ABSTRACT

Novel 2-sulfamoylbenzo[b]thiopenes and derivatives thereof are shown to be useful for the treatment of elevated intraocular pressure in compositions including ophthalmic drops and inserts.

9 Claims, No Drawings

2-SULFAMOYLBENZO(B)THIOPHENE DERIVATIVES PHARMACEUTICAL COMPOSITIONS AND USE

SUMMARY OF THE INVENTION

This is a division of application Ser. No. 600,695, filed Apr. 16, 1984, now U.S. Pat. No. 4,668,697, which is a continuation-in-part of copending application, Ser. No. 547,191 filed Oct. 31, 1983 (abandoned), which is a continuation-in-part of application, Ser. No. 506,092, filed June 20, 1983 (abandoned).

This invention relates to novel 2-sulfamoylbenzo[b]-thiophenes which are useful in the reduction of elevated intraocular pressure. More particularly this invention relates to compounds having the structural formula:

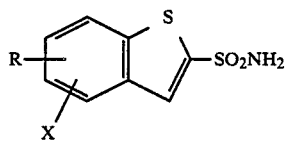

wherein R and X are as hereinafter defined, as well as the pharmaceutically and ophthalmologically acceptable salts thereof. This invention also relates to pharmaceutical compositions for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in European patent applications Nos. 0,070,239 and 0,079,269 and U.S. application, Ser. No. 364,953. The compounds reported therein are 5 (and 6)-hydroxy-2-benzothiazolesulfonamides and acyl esters thereof.

To be an effective and acceptable topical agent, an ophthalmic carbonic anhydrase inhibitor must not only penetrate the ophthalmic tissues to reach the active sites within the eye, but it must also be devoid of those side effects including irritation, allergic reaction and the like which would militate against long term administration.

DETAILED DESCRIPTION OF THE INVENTION

The novel compounds of this invention have structural formula:

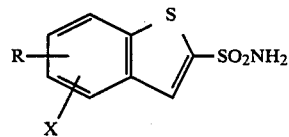

or an ophthalmologically or pharmaceutically acceptable salt thereof, wherein:

X is hydrogen, halo, such as chloro, bromo or fluoro, $C_{1-3}$alkyl, hydroxy or $C_{1-3}$alkoxy; and R is:

(1) hydroxy,
(2) $R_a{}^1$ wherein $R_a{}^1$ is
 (a) $C_{1-18}$ alkyl either straight or branched chain substituted with one or more of
  (i) $C_{3-6}$ cycloalkyl,
  (ii) halo, such as chloro, bromo or fluoro,
  (iii) aryl, wherein the aryl group is carbocyclic such as phenyl or naphthyl, or heterocyclic such as pyridinyl, furanyl, pyrazinyl, morpholinyl, oxazolinyl, dioxolinonyl, imidazolyl, thienyl or the like and wherein the aryl group can be substituted with one or more of $C_{1-10}$ alkyl, halo, $C_{1-4}$ alkoxy, $C_{2-5}$ alkanoyl, or trifluoromethyl,
  (iv) hydroxy,
  (v) $C_{1-3}$ alkoxy,
  (vi) aryl-$C_{1-3}$alkoxy,
  (vii) $C_{1-4}$ alkoxy-$C_{1-3}$alkoxy,
  (viii) amino,
  (ix) $C_{1-3}$ alkyl)amino,
  (x) di($C_{1-3}$ alkyl)amino,
  (xi)

wherein $R^2$ is
(1) HO—,
(2) $M^+O^-$, wherein $M^+$ is a pharmaceutically acceptable cation such as that from an alkali metal, or an ammonium,
(3) $C_{1-10}$ alkoxy,
(4) $R^3R^4N$— wherein $R^3$ and $R^4$ are independently hydrogen, hydroxy, $C_{1-15}$ alkyl, or taken together form a 3–7 membered heterocycle with the nitrogen to which they are attached such as piperidino or pyrrolidino, or
(xii) $C_{2-5}$ alkanoyl;
(b) $C_{3-6}$ cycloalkyl,
(c) $C_{1-18}$ alkyl-$C_{3-6}$ cycloalkyl,
(d) aryl as previously defined,
(e) $R^3R^4N$—
(f) $C_{2-6}$ alkenyl,
(g) aryl-$C_{2-6}$ alkenyl,
(h) $C_{2-6}$ alkynyl, or
(i) heterocyclyl of 5 or 6 members with one or two heteroatoms selected from O, N and S, such as tetrahydropyrrolyl, tetrahydrofuranyl, or imidazolidinyl,
(3) $R_\alpha^1$—O—
(4)

wherein $R^1$ is $R_\alpha^1$ or $C_{1-18}$alkyl,
(5)

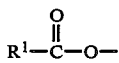

(6)

(7)

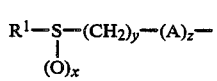

wherein x is 0–2; y is 0–3; z is 0 or 1; and A is a heteroatom such as S, O or N,
(8)

where $R^5$ and $R^6$ are independently:
(a) hydrogen,
(b) $C_{1-18}$ alkyl, either straight or branched chain,
(c) $C_{3-6}$ cycloalkyl,
(d) $C_{3-6}$ cycloalkyl-$C_{1-3}$ alkyl,
(e) aryl-$C_{1-3}$ alkyl wherein the aryl group is either unsubstituted or substituted with one or more of chloro, bromo, fluoro, $C_{1-3}$ alkyl or $C_{1-3}$ alkoxy,
(f)

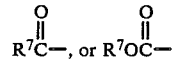

wherein $R^7$ is
(i) $C_{1-18}$ alkyl, either straight or branched chain,
(ii) aryl, either unsubstituted or substituted with one or more of chloro, bromo, fluoro, $C_{1-3}$ alkyl, or $C_{1-3}$ alkoxy,
(iii) aryl-$C_{1-3}$ alkyl wherein the aryl group is either unsubstituted or substituted with one or more of chloro, bromo, fluoro, $C_{1-3}$ alkyl or $C_{1-3}$ alkoxy,
(iv) amino-$C_{1-18}$ alkyl either straight or branched chain; or
(g) $R^5$ and $R^6$ if lower alkyl, are joined together directly or through a heteroatom selected from O or N to form a 5 or 6 membered heterocycle with the nitrogen to which they are attached such as pyrrolidine, piperidine, morpholine, or piperazine,
(9)

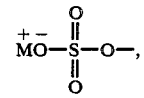

wherein $M^+$ is an ophthalmologically acceptable cation selected from sodium, potassium ammonium, tetra($C_{1-4}$alkyl)ammonium, pyridinium, imidazolium, pralidoxime, and thiamine
(10)

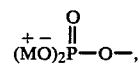

wherein $M^+$ is as previously defined;
(11)

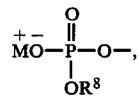

wherein $R^8$ is $C_{1-3}$ alkyl or phenyl-$C_{1-3}$ alkyl; or
(12)

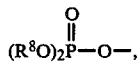

wherein $R^8$ is as previously defined, and the two may be the same or different; and
R and X, joined together, represent methylenedioxy.

In the preferred embodiments of this invention, X is hydrogen and R is

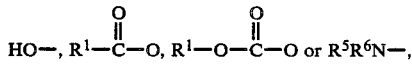

especially wherein $R^1$ is $C_{1-18}$alkyl, and more especially $C_{1-4}$alkyl. It is also preferred that the substituent R be in the 5- or 6-position of the benzo[b]thiophene, especially the 6-position.

Preferred species of this invention are:
5(or 6)-hydroxy-2-sulfamoylbenzo[b]thiophene;
5(or 6)-(2-sulfamoylbenzo[b]thienyl) acetate;
5(or 6)-(2-sulfamoylbenzo[b]thienyl) 2,2-dimethylpropionate;
5(or 6)-(2-sulfamoylbenzo[b]thienyl) 2-methylpropionate.
5(or 6)-(2-sulfamoylbenzo[b]thienyl) 3-methoxycarbonylpropionate;

Representative carbonic anhydrase inhibitors of this invention include:
5(or 6)-hydroxy-2-sulfamoylbenzo[b]thiophene;
5(or 6)-(2-sulfamoylbenzo[b]thienyl) benzoate;
5(or 6)-(2-sulfamoylbenzo[b]thienyl) propionate;
5(or 6)-(2-sulfamoylbenzo[b]thienyl) butyrate;
5(or 6)-(2-sulfamoylbenzo[b]thienyl) 2,2-dimethylpropionate;
5(or 6)-(2-sulfamoylbenzo[b]thienyl) octanoate
5(or 6)-(2-sulfamoylbenzo[b]thienyl) dodecanoate;
5(or 6)-(2-sulfamoylbenzo[b]thienyl) 4,4-dimethylcyclohexane carboxylate;
5(or 6)-(2-sulfamoylbenzo[b]thienyl) 3-chloro-2,2-dimethylpropionate;
5(or 6)-(2-sulfamoylbenzo[b]thienyl) 4-methylbenzoate;
5(or 6)-(2-sulfamoylbenzo[b]thienyl) 4-chlorobenzoate;
5(or 6)-(2-sulfamoylbenzo[b]thienyl) 4-methoxybenzoate;
5(or 6)-(2-sulfamoylbenzo[b]thienyl) 2-(4-chlorophenyl)acetate;
5(or 6)-(2-sulfamoylbenzo[b]thienyl) 3-(4-ethylphenyl)propionate;
5(or 6)-(2-sulfamoylbenzo[b]thienyl) 3-hydroxy-2,2-dimethylpropionate;
5(or 6)-(2-sulfamoylbenzo[b]thienyl) 4-aminobutyrate HCl;
5(or 6)-(2-sulfamoylbenzo[b]thienyl) acrylate;
5(or 6)-(2-sulfamoylbenzo[b]thienyl) crotonate;
5(or 6)-(2-sulfamoylbenzo[b]thienyl) propiolate;
5(or 6)-(2-sulfamoylbenzo[b]thienyl) 3-phenyl-2-propenoate;
5(or 6)-(2-sulfamoylbenzo[b]thienyl) cyclopentaneacetate;
5(or 6)-(2-sulfamoylbenzo[b]thienyl) phenylacetate;
5(or 6)-(2-sulfamoylbenzo[b]thienyl) cyclohexanecarboxylate;
5(or 6)-(2-sulfamoylbenzo[b]thienyl) acetate;
5(or 6)-(2-sulfamoylbenzo[b]thienyl) 3-carboxypropionate;
5(or 6)-(2-sulfamoylbenzo[b]thienyl) 3-carboxypropionate, sodium salt;
5(or 6)-(2-sulfamoylbenzo[b]thienyl) 2-ethoxycarbonylacetate;
5(or 6)-(2-sulfamoylbenzo[b]thienyl) acetoacetate;
5(or 6)-(2-sulfamoylbenzo[b]thienyl) 3-aminocarbonylpropionate;
5(or 6)-(2-sulfamoylbenzo[b]thienyl) N-acetylpiperidine-4-carboxylate;
5(or 6)-(2-sulfamoylbenzo[b]thienyl) nicotinoate;
5(or 6)-(2-sulfamoylbenzo[b]thienyl) 1-methyl-4-imidazolylacetate;
5(or 6)-(2-sulfamoylbenzo[b]thienyl) 2-methoxybutyrate;
5(or 6)-(2-sulfamoylbenzo[b]thienyl) 2-methoxysuccinate;
5(or 6)-(2-sulfamoyl-benzo[b]thienyl) phenyl carbonate;
5(or 6)-(2-sulfamoyl-benzo[b]thienyl) ethyl carbonate;
5(or 6)-(2-sulfamoyl-benzo[b]thienyl) propyl carbonate;
5(or 6)-(2-sulfamoyl-benzo[b]thienyl) 1,1-dimethylethyl carbonate;
5(or 6)-(2-sulfamoyl-benzo[b]thienyl) n-heptyl carbonate;
5(or 6)-(2-sulfamoyl-benzo[b]thienyl) undecanyl carbonate;
5(or 6)-(2-sulfamoyl-benzo[b]thienyl) 4,4-dimethylcyclohexyl carbonate;
5(or 6)-(2-sulfamoyl-benzo[b]thienyl) 2-chloro-1,1-dimethylethyl carbonate;
5(or 6)-(2-sulfamoyl-benzo[b]thienyl) 4-methylphenyl carbonate;
5(or 6)-(2-sulfamoyl-benzo[b]thienyl) 4-chlorophenyl carbonate;
5(or 6)-(2-sulfamoyl-benzo[b]thienyl) 4-methoxyphenyl carbonate;
5(or 6)-(2-sulfamoyl-benzo[b]thienyl)-4-chlorobenzyl carbonate;
5(or 6)-(2-sulfamoyl-benzo[b]thienyl) 2-(4-ethylphenyl)ethyl carbonate;
5(or 6)-(2-sulfamoyl-benzo[b]thienyl) 2-methylpropyl carbonate;
5(or 6)-(2-sulfamoyl-benzo[b]thienyl) allyl carbonate;
5(or 6)-(2-sulfamoylbenzo[b]thienyl) 2-propynyl carbonate;
5(or 6)-(2-sulfamoyl-benzo[b]thienyl) 3-phenyl-2-propenyl carbonate;
5(or 6)-(2-sulfamoyl-benzo[b]thienyl) cyclopentylmethyl carbonate;
5(or 6)-(2-sulfamoyl-benzo[b]thienyl) benzyl carbonate;
5(or 6)-(2-sulfamoyl-benzo[b]thienyl) cyclohexyl carbonate;
5(or 6)-(2-sulfamoyl-benzo[b]thienyl) methyl carbonate;
5(or 6)-amino-2-sulfamoylbenzo[b]thiophene;
5(or 6)-ethylamino-2-sulfamoylbenzo[b]thiophene;
5(or 6)-diethylamino-2-sulfamoylbenzo[b]thiophene;
5(or 6)-[(1-methylethyl)amino]-2-sulfamoylbenzo[b]thiophene;
5(or 6)-[N-ethyl-N-(2-propyl)amino]-2-sulfamoylbenzo[b]thiophene;
5(or 6)-[(N-benzyl-N-ethyl)amino]-2-sulfamoylbenzo[b]thiophene;
5(or 6)-cyclohexylamino-2-sulfamoylbenzo[b]thiophene;
5(or 6)-cyclopentylmethylamino-2-sulfamoylbenzo[b]thiophene;
5(or 6)-pivaloylamino-2-sulfamoylbenzo[b]thiophene;
5(or 6)-[N-methyl-N-pivaloyl)amino]-2-sulfamoylbenzo[b]thiophene;
5(or 6)-pivaloyloxycarbonylamino-2-sulfamoylbenzo[b]thiophene;
5(or 6)-acetylamino-2-sulfamoylbenzo[b]thiophene;
5(or 6)-butyrylamino-2-sulfamoylbenzo[b]thiophene;
5(or 6)-benzoylamino-2-sulfamoylbenzo[b]thiophene;
5(or 6)-[(4-methylbenzoyl)amino]-2-sulfamoylbenzo[b]thiophene;
5(or 6)-[(4-fluorobenzoyl)amino]-2-sulfamoylbenzo[b]thiophene;
5(or 6)-(4-methoxybenzoyl)amino-2-sulfamoylbenzo[b]thiophene;
5(or 6)-nicotinoylamino-2-sulfamoylbenzo[b]thiophene;
5(or 6)-thienylcarbonylamino-2-sulfamoylbenzo[b]thiophene;
5(or 6)-alanylamino)-2-sulfamoylbenzo[b]thiophene;
5(or 6)-(N-ethyl-N-hydroxy)amino-2-sulfamoylbenzo[b]thiophene;

5(or 6)-(N-methyl-N-methoxy)amino-2-sulfamoylbenzo[b]thiophene;
5(or 6)-(1-morpholino)-2-sulfamoylbenzo[b]thiophene;
2-sulfamoylbenzo[b]thiophene-6(or 5)-acetic acid;
2-sulfamoylbenzo[b]thiophene-6(or 5)-propionic acid;
5(or 6)-(2-hydroxyethyl)-2-sulfamoylbenzo[b]thiophene;
5(or 6)-(2,3-dihydroxypropoxy)-2-sulfamoylbenzo[b]thiophene;
5(or 6)-(dioxolin-2-one-4-ylmethoxy)-2-sulfamoylbenzo[b]thiophene;
5(or 6)-(5-oxazolinylmethoxy)-2-sulfamoylbenzo[b]thiophene;
5(or 6)-(1-methylimidazol-4-yloxy)-2-sulfamoylbenzo[b]thiophene;
5(or 6)-furfuryl-2-sulfamoylbenzo[b]thiophene;
5(or 6)-(2-morpholinylethyl)-2-sulfamoylbenzo[b]thiophene;
5(or 6)-morpholinylmethyl-2-sulfamoylbenzo[b]thiophene;
5(or 6)-hydroxymethyl-2-sulfamoylbenzo[b]thiophene;
5(or 6)-(acetyloxymethyl)-2-sulfamoylbenzo[b]thiophene;
5(or 6)-(2-acetyloxyethyl)-2-sulfamoylbenzo[b]thiophene;
5(or 6)-benzoyl-2-sulfamoylbenzo[b]thiophene;
5(or 6)-propionyl-2-sulfamoylbenzo[b]thiophene;
5(or 6)-butyryl-2-sulfamoylbenzo[b]thiophene;
5(or 6)-(2,2-dimethylpropionyl)-2-sulfamoylbenzo[b]thiophene;
5(or 6)-octanoyl-2-sulfamoylbenzo[b]thiophene;
5(or 6)-dodecanoyl-2-sulfamoylbenzo[b]thiophene;
5(or 6)-(4,4-dimethylcyclohexanecarbonyl)-2-sulfamoylbenzo[b]thiophene;
5(or 6)-(3-chloro-2,2-dimethylpropionyl)-2-sulfamoylbenzo[b]thiophene;
5(or 6)-(2-methylbenzoyl)-2-sulfamoylbenzo[b]thiophene;
5(or 6)-(4-chlorobenzoyl)-2-sulfamoylbenzo[b]thiophene;
5(or 6)-(4-methoxybenzoyl)-2-sulfamoylbenzo[b]thiophene;
5(or 6)-(4-chlorophenylacetyl)-2-sulfamoylbenzo[b]thiophene;
5(or 6)-[3-(4-ethylphenyl)propionyl)]-2-sulfamoylbenzo[b]thiophene;
5(or 6)-(3-hydroxy-2,2-dimethylpropionyl)-2-sulfamoylbenzo[b]thiophene;
5(or 6)-(4-aminobutyryl)-2-sulfamoylbenzo[b]thiophene;
5(or 6)-(acryloyl)-2-sulfamoylbenzo[b]thiophene;
5(or 6)-(crotonyl)-2-sulfamoylbenzo[b]thiophene;
5(or 6)-propiolyl-2-sulfamoylbenzo[b]thiophene;
5(or 6)-(3-phenyl-2-propenoyl)-2-sulfamoylbenzo[b]thiophene;
5(or 6)-cyclopentaneacetyl-2-sulfamoylbenzo[b]thiophene;
5(or 6)-phenylacetyl-2-sulfamoylbenzo[b]thiophene;
5(or 6)-cyclohexanecarbonyl-2-sulfamoylbenzo[b]thiophene;
5(or 6)-acetyl-2-sulfamoylbenzo[b]thiophene;
5(or 6)-(3-carboxypropionyl)-2-sulfamoylbenzo[b]thiophene;
5(or 6)-ethoxycarbonylacetyl-2-sulfamoylbenzo[b]thiophene;
5(or 6)-acetoacetyl-2-sulfamoylbenzo[b]thiophene;
5(or 6)-aminocarbonylpropionyl)-2-sulfamoylbenzo[b]thiophene;
5(or 6)-(N-acetylpiperidine-4-carbonyl)-2-sulfamoylbenzo[b]thiophene;
5(or 6)-(4-imidazolyl)-2-sulfamoylbenzo[b]thiophene;
5(or 6)-pyrazinyl-2-sulfamoylbenzo[b]thiophene;
5(or 6)-(4-imidazolylcarbonyl)-2-sulfamoylbenzo[b]thiophene;
5(or 6)-(4-imidazolylsulfonyl)-2-sulfamoylbenzo[b]thiophene;
5(or 6)-(trifluoromethylsulfonyl)-2-sulfamoylbenzo[b]thiophene;
5-[N-(tertbutoxycarbonyl)glycyloxy]-2-sulfamoylbenzo[b]thiophene, m.p. 168°–170° C. (dec);
5-(2-hydroxyethoxy)-2-sulfamoylbenzo[b]thiophene; m.p. 127°–128° C.;
5-(glycyloxy)-2-sulfamoylbenzo[b]thiophene hydrochloride, m.p. 223°–233° C.;
5-(N,N-Dimethylcarbamoylmethoxy)-2-sulfamoylbenzo[b]thiophene, m.p. 259°–261° C.;
5-(L-prolyloxy)-2-sulfamoylbenzo[b]thiophene hydrochloride, m.p. 229°–231° C.;
5-(2-dimethylaminoethoxy)-2-sulfamoylbenzo[b]thiophene, m.p. 204.5°–205.5° C.;
5-(2-methoxyethoxy)-2-sulfamoylbenzo[b]thiophene, m.p. 153°–154° C.;
5-[2-(isopropoxy)ethoxymethyl]-2-sulfamoylbenzo[b]thiophene, m.p. 65°–69° C.;
5-(2-dimethylaminoethyl)-2-sulfamoylbenzo[b]thiophene, m.p. 208°–209° C.;
6-(1-triphenylmethylimidazol-4-yl)methoxy-2-sulfamoylbenzo[b]thiophene, m.p. 238°–239° C.;
6-(1-imidazol-4-yl)-2-sulfamoylbenzo[b]thiophene hydrochloride, m.p. 221°–223° C.

6-Methoxy-2-sulfamoylbenzo[b]thiophene, a novel compound and a key intermediate for many of the other novel compounds of this invention, is obtained by reacting bromoacetaldehyde diethyl acetal in the presence of a base with at least a molar equivalent of m-methoxybenzenethiol in a suitable inert solvent, preferably acetone, at a temperature extending to reflux. After reaction is essentially complete the 1-[(2,2-diethoxy)ethylthio]-3-methoxybenzene obtained is collected and suitably extracted, washed and dried. The dried product is then slowly added to at least a molar equivalent of the catalyst boron trifluoride.etherate in an inert solvent such as chloroform at a temperature extending to reflux until reaction is essentially completed. Preferably the reaction is conducted under an inert atmosphere such as nitrogen. A mixture of 6-methoxybenzo[b]thiophene and 4-methoxybenzo[b]thiophene in an approximate ratio of 10:1 is obtained upon evaporation of the solvent. The mixture is treated with at least a molar equivalent of n-butyl lithium in an inert solvent such as tetrahydrofuran at a reduced temperature, preferably below −10° C., most suitably at −70° C. Sulfur dioxide gas is then passed over the solution at a rate such that the reaction mixture does not exceed a temperature of −10° C. After the reaction is complete, the solvents are removed and the product reacted with at least one molar equivalent of N-chlorosuccinimide at reduced temperature, generally 0° C. or less. The mixture of 4- and 6-methoxybenzo[b]thiophene-2-sulfonyl chlorides that is produced is treated with concentrated aqueous ammonia. The resulting mixture of 4- and 6-methoxy-2-sulfamoylbenzo[b]thiophenes is then collected and the isomers are separated by fractional crystallization. Each is further purified by reprecipitation from aqueous base by treatment with acid and/or recrystallization from an appropriate solvent.

The novel process for preparing the compounds wherein R is hydroxy comprises treatment of a methoxy-2-sulfamoylbenzo[b]thiophene with at least an equimolar amount of pyridine hydrochloride at a temperature from about the fusion point to about 200° C., and preferably from about 180°–190° C. for from about 1 to 4 hours, preferably about 2 hours, until the reaction is substantially complete.

The novel process to prepare those compounds wherein R is

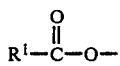

is represented by the following reaction scheme:

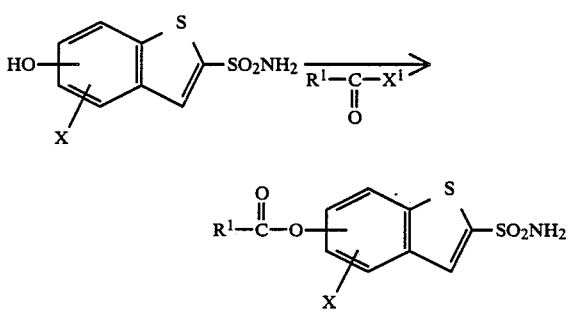

where $R^1$ has the meanings hereinbefore designated, and $X^1$ is chloro, bromo, iodo,

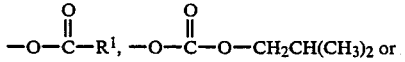

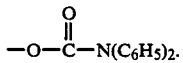

Generally equimolar amounts of the hydroxy-2-sulfamoylbenzo[b]thiophene and

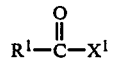

are employed, although use of an excess of the more readily available reactant is satisfactory.

The reaction is conducted in a suitable, inert solvent such as acetone, dimethylformamide, pyridine, ethyl acetate, tetrahydrofuran or benzene and the like with at least an equimolar amount of a hydrohalide acceptor when the acylating agent is an acyl halide or with a carboxylic acid acceptor when the acylating agent is an acid anhydride. Bases such as triethylamine, pyridine and the like may be employed for this purpose.

The reaction may be conducted with or without a catalyst at temperatures of from 0° C. to the boiling point of the solvent used but preferably from about 15° C. to 50° C.

When a catalyst is employed, a 4,4-dialkylaminopyridine such as 4-dimethylaminopyridine or 4-pyrrolidinopyridine is preferred.

The compounds wherein R is

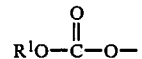

of this invention are most suitably prepared by reacting a compound

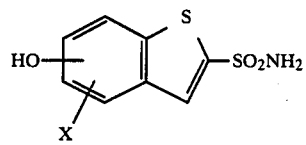

with an appropriate haloformate, particularly a chloroformate of the formula:

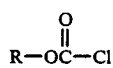

or a bis carbonate of the formula:

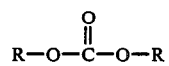

The reaction is conducted in a suitable solvent such as dimethylformamide, pyridine, acetone, ethyl acetate, tetrahydrofuran or benzene and the like with at least an equimolar amount of a hydrohalide acceptor. Bases such as triethylamine, pyridine and the like may be employed for this purpose.

The reaction may be conducted with or without a catalyst at temperatures of from 0° C. to the boiling point of the solvent used but preferably from 15° C. to 50° C.

When a catalyst is employed, triethylamine or a 4,4-dialkylaminopyridine such as 4-dimethylaminopyridine or 4-pyrrolidinopyridine is preferred.

In the novel process of this invention for preparing the ethers of hydroxy-2-sulfamoylbenzo[b]thiophenes, the hydroxy compound is treated with an "alkylating" agent of formula $R^1$—$X^2$ wherein $X^2$ is a halide such as chloride, bromide or iodide, or other good leaving group such as mesylate, tosylate or benzenesulfonate in a suitable solvent such as dimethyl formamide, hexamethyl phosphoramide, or the like in the presence of a base such as an alkali metal alkoxide, preferably sodium methoxide, at about 0° C. to 35° C., usually about room temperature for about 10 to 30 hours.

An alternate synthesis of ethers comprises protecting the sulfonamide group as an N,N-disubstituted formamidine which is removed after formation of the desired ether. The formamidine derivative is prepared by adding, for example, N,N-dimethylformamide dimethylacetal to a suspension of the hydroxy-2-sulfamoylbenzo[b]thiophene in an inert organic solvent such as acetonitrile at about −10° to +35° C., preferably room temperature for about 0.5 to about 3 hours.

The ethers are then readily prepared by treating the hydroxy compound with the "alkylating" agent, $R^1$—$X^2$, in a solvent such as dimethyl sulfoxide, preferably in the presence of an acid acceptor such as potassium carbonate or the like, pyridine or the like or basic ion exchange resin. The reaction is conducted at about 25° to 100° C., preferably about 60° C., for about 10 to 36 hours, preferably about 18 hours.

The protecting group is then removed from the sulfonamide by treating the compound with dilute alkali such as 2N sodium hydroxide at about 20° to 60° C., preferably about 40° C. for about 0.5 to 3 hours, preferably about 1 hour. Also, 6N HCl at about 100° C. for 2–5 hours can be used to effect the desired deprotection.

The novel compounds of this invention with no substituent, i.e. R=H and those carrying fairly stable substituents such as wherein R is $R^1$ and $R^1$ is alkyl, cycloalkyl, cycloalkyl-alkyl, alkylcycloalkyl, alkoxyalkyl, alkenyl; R is $R^1$—O— wherein $R^1$ is as defined above; R is $R^5R^6$—N— wherein $R^5$ and $R^6$ are not hydrogen are conveniently prepared by formation of the sulfonamide group on the intact benzo[b]thiophene moiety. This is accomplished by the procedure described earlier for preparation of 6-methoxy-2-sulfamoylbenzo[b]thiophene.

The O-sulfates of this invention are prepared by reacting an hydroxy-2-sulfamoylbenzo[b]thiophene with sulfamic acid in pyridine at elevated temperatures (about 50° to the boiling point) for about 18 to 48 hours to provide the ammonium salt followed, if desired, by titration with hydroxides of the formula MOH to provide the other salts.

Similarly the O-phosphates of this invention are prepared by treatment of a hydroxy-2-sulfamoylbenzo[b]-thiophene with phosphorus oxychloride, an alkyl dichlorophosphate or a dialkyl chlorophosphate in pyridine or similar basic solvent at about −5° to +5° C. for about 0.25 to 1.0 hour.

EXAMPLE 1

6-Hydroxy-2-sulfamoylbenzo[b]thiophene

Step A: Preparation of 1-[(2,2-diethoxy)ethylthio]-3-methoxybenzene

Bromoacetaldehyde diethyl acetal (16.5 ml, 0.11 mol) was added dropwise to a mixture of m-methoxybenzenethiol (15.0 ml, 0.12 mol) and $K_2CO_3$ (16.6 g, 0.12 mol) in acetone (150 ml) at room temperature. The reaction mixture was stirred for 16 hours and then filtered. The solid was washed with acetone, and the combined filtrate and washes were concentrated in vacuo. The residue was diluted with $H_2O$ and extracted with $Et_2O$. The $Et_2O$ extracts were washed with 0.5M KOH, $H_2O$, and brine, dried over $Na_2SO_4$, filtered, and concentrated in vacuo to give 27.4 g of 1-[(2,2-diethoxy)ethylthio]-3-methoxybenzene as a dark yellow oil. 'H NMR, δ: (CDCl$_3$): 1.18 (6H, t, —OCH$_2$CH$_3$); 3.13 (2H, d, —SCH—); 3.43–3.73 (4H, m, —OCH$_2$CH$_3$); 3.77 (3H, s, —OCH$_3$); 4.67 (1H, t, —SCH$_2$CH—); 6.60–7.27 (4H, m, aromatics).

Step B: Preparation of 6-methoxybenzo[b]thiophene

A solution of 1-[(2,2-diethoxy)ethylthio]-3-methoxybenzene (13.0 g, 0.051 mol) in CH$_2$Cl$_2$ (100 ml) was added dropwise to a solution of BF$_3$.Et$_2$O (6.7 ml, 0.054 mol) in CH$_2$Cl$_2$ (1000 ml) at room temperature under a nitrogen atmosphere. The reaction mixture was stirred for 0.5 hours, treated with aqueous NaHCO$_3$ solution, and stirred until both phases were clear. The CH$_2$Cl$_2$ layer was separated, and the aqueous layer was extracted with CH$_2$Cl$_2$. The combined organic extracts were dried over Na$_2$SO$_4$, filtered, and concentrated in vacuo to give 8.68 g of an approximately 10:1 mixture of 6- and 4-methoxybenzo[b]thiophene as a dark brown oil. Purification by vacuum distillation (bp=65°–7° C. at 0.3 mmHg) gave 5.58 g of pale yellow oil. Major isomer: 'H NMR, δ: (CDCl$_3$): 3.85 (3H, s, —OCH$_3$); 6.98 (1H, dd, J=4.5, H$_5$); 7.23 (2H, s, H$_2$, H$_3$); 7.35 (1H, d, J=1.5, H$_7$); 7.68 (1H, d, J=4.5, H$_4$).

Step C: Preparation of 6-methoxy-2-sulfamoylbenzo[b]thiophene

A solution of the mixture of 6- and 4-methoxybenzo[b]thiophene (6.04 g, 37 mmol) in 40 ml of dry THF was treated with n-butyl lithium (27 ml of a 1.64M solution in hexane, 44 mmol) at −20° C. After stirring for 1 hour at −20° C., SO$_2$ gas was passed over the surface of the solution at such a rate to maintain the internal temperature of the reaction at −10° C. The reaction is judged complete when the temperature falls and the reaction mixture has changed from red to a yellow suspension. The solvents were evaporated in vacuo and the residue dissolved in 75 ml saturated NaHCO$_3$ solution. After cooling to 0° C., N-chlorosuccinimide (6.5 g, 48 mmol) was added in four portions over 5 minutes. A solid precipitate was collected by filtration. The aqueous filtrate was extracted with ethyl acetate and the organic phase washed with brine and dried. The solvent was evaporated to yield an oil. The oil and the initial solid precipitate were combined in a small volume of acetone and added to a solution of 25 ml of NH$_4$OH in 100 ml of acetone. After 30 minutes, the solvents were evaporated and the residue was partitioned between 100 ml 1N KOH and ether (100 ml). The ether layer was extracted again with 1N KOH (2×50 ml). The combined basic extract was neutralized with concentrated HCl. The precipitate was extracted into ethyl acetate. The organic extract was washed with brine and dried. Evaporation of the solvent gave 8.11 g of a tan solid m.p. 155°–160° C. Recrystallization from dichloroethane affords the pure 6-methoxy isomer m.p. 166°–167° C. 'H-NMR δ(DMSO-d$_6$): 7.85 (1H, dd, 5=9), 7.77 (1H, s), 7.72 (2H, br s), 7.60 (1H, dd, J=2), 7.05 (1H, dd, J=9 and 2), 4.81 (3H, s).

Analysis Calc'd for C$_9$H$_9$NO$_3$S$_2$: C, 44.43; H, 3.73; N, 5.76. Found: C, 44.61; H, 3.75; N, 5.82.

Concentration of the mother liquors from the recrystallization afforded a second crop of crystals which was largely 4-methoxy-2-sulfamoylbenzo[b]thiophene. A second crystallization of this material gave the pure compound, m.p. 180°–182° C. 'H-NMR δ: (DMSO-d$_6$): 7.83 (1H, brs), 7.80 (1H, s), 7.60 (1H, d), 7.44 (1H, t), 6.95 (1H, d), 3.92 (3H, s).

Analysis calculated for C$_9$H$_9$NO$_3$S$_2$: C, 44.43; H, 3.73; N, 5.76. Found: C, 44.31; H, 3.62; N, 5.73.

Employing the procedures substantially as described in Example 1, Steps A, B and C, except for the separation of isomers in Step C, and starting with 3,4-methylenedioxybenzenethiol, there is produced in sequence:

1-[(2,2-diethoxy)ethylthio]-3,4-methylenedioxybenzene; 5,6-methylenedioxybenzo[b]thiophene; and 5,6-methylenedioxy-2-sulfamoylbenzo[b]thiophene.

Step D: Preparation of 6-Hydroxy-2-sulfamoylbenzo[b]thiophene

A mixture of 3.6 g of 6-methoxy-2-sulfamoylbenzo[b]thiophene and 37 g of pyridine hydrochloride was heated to 180°–190° C. for 2 hours. After cooling, the solid was dissolved in 200 ml water. The product was isolated by extraction with ethyl acetate (3×75 ml). The organic extract was washed with dilute HCl and brine, and dried over Na$_2$SO$_4$. The solvent was evaporated yielding 3.2 g of a brown solid. The solid was dissolved in 200 ml acetone and treated with 1.3 g of decolorizing carbon. The solution was filtered and the solvent evaporated to yield 2.8 g of a yellow solid. The solid was dissolved in a minimal volume of ethyl acetate and triturated with hexane. A white solid m.p. 211°–214° C., weighing 1.70 g was obtained. 'H-NMR δ(DMSO-d$_6$): 10.02 (1H, br s) 7.81 (1H, d, J=9), 7.75 (1H, s), 7.71 (2H, s), 7.33 (1H, d, J=2); 6.96 (1H, dd, J=9 and 2). Further recrystallization from water or nitromethane provides material of greater than 99.9% purity, m.p. 215°–216° C.

Analysis: Calc'd for $C_8H_7NO_3S_2$: C, 41.91; H, 3.08; N, 6.11. Found: C, 41.87; H, 2.91; N, 6.17.

Demethylation of the 4-methoxy isomer occurs under the same conditions. A single recrystallization from water gave tan needles m.p. 212–213. 'H-NMR, δ(acetone d$_6$): 9.3 (1H, br s), 7.96 (1H, s), 7.4 (2H, m), 6.9 (2H, br s and 1H, dd).

Analysis calculated for $C_8H_7NO_3S_2$: C, 41.91; H, 3.08; N, 6.11. Found: C, 41.84; H, 2.94; N, 6.21.

Employing the procedures substantially as described in Example 1, Steps A, B, C and D, but substituting for the m-methoxybenzenethiol used in Step A thereof, an approximately equimolar amount of:
(a) 2,4-dimethoxybenzenethiol;
(b) 2,5-dimethoxybenzenethiol;
(c) 3,4-dimethoxybenzenethiol;
(d) 3-methyl-4-methoxybenzenethiol; and
(e) 3-methoxy-4-methylbenzenethiol; there are produced in Step B:
(a) 5,7-dimethoxybenzo[b]thiophene;
(b) 4,7-dimethoxybenzo[b]thiophene;
(c) 5,6-dimethoxybenzo[b]thiophene and 4,5-dimethoxybenzo[b]thiophene;
(d) 5-methoxy-6-methylbenzo[b]thiophene; and
(e) 5-methyl-6-methoxybenzo[b]thiophene; in Step C:
(a) 5,7-dimethoxy-2-sulfamoylbenzo[b]thiophene;
(b) 4,7-dimethoxy-2-sulfamoylbenzo[b]thiophene;
(c) 5,6-dimethoxy-2-sulfamoylbenzo[b]thiophene and 4,5-dimethoxy-2-sulfamoylbenzo[b]thiophene;
(d) 5-methoxy-6-methyl-2-sulfamoylbenzo[b]thiophene; and
(e) 5-methyl-6-methoxy-2-sulfamoylbenzo[b]thiophene; and, in Step D:
(a) 5,7-dihydroxy-2-sulfamoylbenzo[b]thiophene;
(b) 4,7-dihydroxy-2-sulfamoylbenzo[b]thiophene;
(c) 5,6-dihydroxy-2-sulfamoylbenzo[b]thiophene and 4,5-dihydroxy-2-sulfamoylbenzo[b]thiophene;
(d) 5-hydroxy-6-methyl-2-sulfamoylbenzo[b]thiophene; and
(e) 6-hydroxy-5-methyl-2-sulfamoylbenzo[b]thiophene.

EXAMPLE 2

6-(2-Sulfamoylbenzo[b]thienyl) 2,2-Dimethylpropionate

To a solution of 6-hydroxy-2-sulfamoylbenzo[b]thiophene (125 mg, 0.54 mmol) in 4 ml of THF was added 0.16 ml of Et$_3$N and 0.24 ml of pivalic anhydride (1.18 mmol). The reaction mixture was stirred for 18 hours at room temperature. The mixture was poured into NaHCO$_3$ solution and extracted with ethyl acetate. The organic extract was washed with brine and dried (Na$_2$SO$_4$). After treating with charcoal and filtering the produce was obtained by trituration with hexane as white crystals, m.p. 165°–167° C. The yield was 58 mg. 'H-NMR, δ(CDCl$_3$): 7.92 (1H, d, J=9); 7.91 (1H, s); 7.58 (1H, d, 5=1); 7.2 (1H, dd, J=9 and 2); 1.37 (9H, s).

Analysis Calc'd for $C_{13}H_{15}NO_4S_2$: C, 49.82; H, 4.82; N, 4.47. Found: C, 49.63; H, 4.86; N, 4.52.

EXAMPLE 3

6-(2-Sulfamoylbenzo[b]thienyl) 2-Methylpropionate

To a stirred solution of 2.00 g of 6-hydroxy-2-sulfamoylbenzo[b]thiophene in 20 ml of dry acetone was added 1.3 ml of Et$_3$N (9.3 mmol) followed by 0.96 ml of isobutyryl chloride (8.8 mmol) dropwise, with stirring at 0°. After twenty minutes the suspension was partitioned between EtOAc and NaHCO$_3$ solution. The organic phase was washed with brine and dried (Na$_2$SO$_4$). Evaporation of the solvent gave 2.77 g of a white solid. Recrystallization from ethyl acetate/hexane gave 1.32 g of white crystals, m.p. 164°–165° C. 'H-NMR, δ(DMSO): 8.05 (1H, d, J=9); 7.93 (1H, s); 7.87 (3H, m); 7.25 (1H, dd, J=9 and 2); 3.84 (1H, m); 1.23 (6H, d, J=7).

Analysis Calc'd for $C_{12}H_{13}NO_4S_2$: C, 48.15; H, 4.30; N, 4.68. Found: C, 47.99; H, 4.33; N, 4.79.

EXAMPLE 4

6-(2-Sulfamoylbenzo[b]thienyl) Acetate

A solution of 6-hydroxy-2-benzothiophenesulfonamide (2.5 g, 0.0109 mole) in acetone (45 ml) at −5° was treated with triethylamine (1.2133 g; 0.01199 mole). Then a solution of acetyl chloride (0.9413 g, 0.01199 mole) in acetone (5 ml) was added, dropwise, during 15 minutes at −5° C. After 15 minutes, the reaction mixture was filtered to remove the precipitated triethylamine hydrochloride. The filtrate was evaporated in vacuo to give an off white solid. This solid was dissolved in ethyl acetate, washed with a small quantity of water and saturated sodium chloride solution and dried over sodium sulfate. Removal of solvent in vacuo gave an off-white solid. The yield was 2.98 g, m.p. 120°–133° C. Recrystallization from 1,2-dichloroethane gave the title compound as white prisms, m.p. 150°–151° C.

Anal. Calc'd. for $C_{10}H_9NO_4S_2$: C, 44.27; H, 3.34; N, 5.16. Found: C, 44.00; H, 3.48; N, 5.19.

Employing the procedure described in the above Examples 2–4, but substituting for the acid chloride starting material used therein, a substantially equivalent molar amount of the acid chlorides described in Table I, there are produced the acyloxy-2-sulfamoylbenzo[b]thiophenes also described in Table I in accordance with the following reaction scheme:

TABLE I

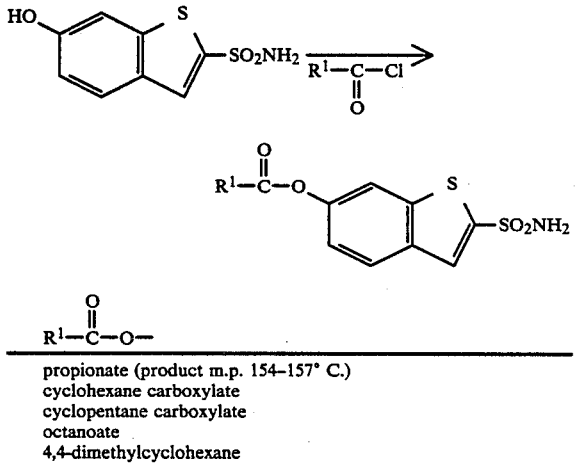

propionate (product m.p. 154–157° C.)
cyclohexane carboxylate
cyclopentane carboxylate
octanoate
4,4-dimethylcyclohexane

TABLE I-continued

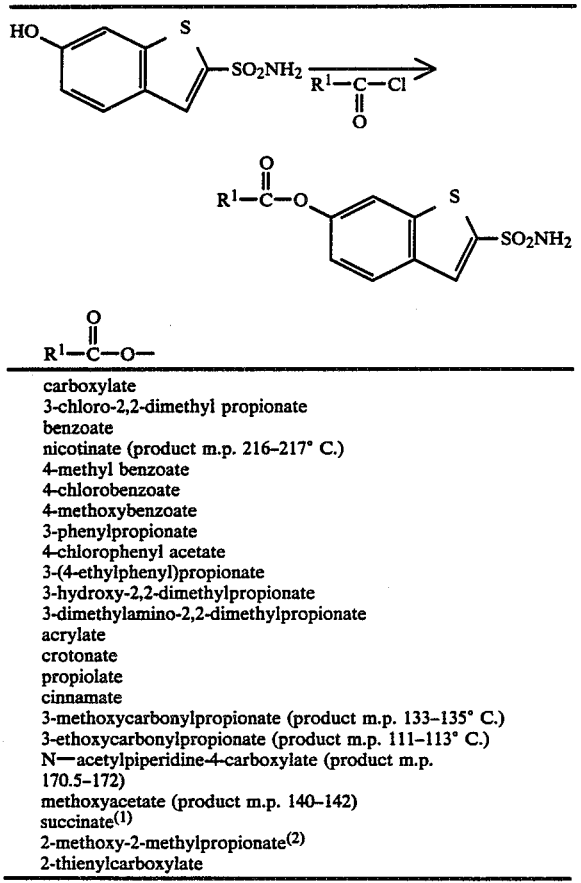

| $R^1-\overset{O}{\underset{\|}{C}}-O-$ |
|---|
| carboxylate |
| 3-chloro-2,2-dimethyl propionate |
| benzoate |
| nicotinate (product m.p. 216–217° C.) |
| 4-methyl benzoate |
| 4-chlorobenzoate |
| 4-methoxybenzoate |
| 3-phenylpropionate |
| 4-chlorophenyl acetate |
| 3-(4-ethylphenyl)propionate |
| 3-hydroxy-2,2-dimethylpropionate |
| 3-dimethylamino-2,2-dimethylpropionate |
| acrylate |
| crotonate |
| propiolate |
| cinnamate |
| 3-methoxycarbonylpropionate (product m.p. 133–135° C.) |
| 3-ethoxycarbonylpropionate (product m.p. 111–113° C.) |
| N—acetylpiperidine-4-carboxylate (product m.p. 170.5–172) |
| methoxyacetate (product m.p. 140–142) |
| succinate[1] |
| 2-methoxy-2-methylpropionate[2] |
| 2-thienylcarboxylate |

[1]acylating reagent is succinic anhydride
[2]acylating reagent is 2-methoxy-2-methylpropionic N,N—diphenyl carbamic anhydride

EXAMPLE 5

5-Hydroxy-2-sulfamoylbenzo[b]thiophene

Step A: Preparation of
5-Methoxy-2-sulfamoylbenzo[b]thiophene

A solution of 5-methoxybenzo[b]thiophene (9.50 g., 0.058 m), in dry tetrahydrofuran (60 ml) was cooled to −20° C. under nitrogen and 1.6M n-butyl lithium in hexane (40 ml, 0.064 m) was added over 20 minutes, maintaining the temperature at −20° to −15° C. After stirring at −20° C. for 1 hour, sulfur dioxide was passed over the surface of the reaction mixture for 45 minutes while keeping the temperature at −15° to −5° C. while stirring vigorously. Ether (100 ml) was added and the precipitate was collected and dried under vacuum at ambient temperature. The solid was suspended in methylene chloride (105 ml) and the mixture was cooled to 0° C. and stirred while N-chlorosuccinimide (18.55 g, 0.064 m) was added over 10 minutes. After stirring at ambient temperature for 2 hours, the mixture was filtered and the solid was washed with methylene chloride. The combined filtrate and washings were concentrated under reduced pressure below 30° C. The solid residue was dissolved in acetone (105 ml), the solution was cooled to 0° C. and concentrated ammonium hydroxide (50 ml) was added over 10 minutes. After stirring at ambient temperature for 30 minutes, the solvent was evaporated under reduced pressure. The residue was dissolved in 0.5M potassium hydroxide solution (370 ml), filtered and the filtrate was acidified with 6N HCl. The product was collected and dried at 70° C. under vacuum to yield 12.11 g (86%) of material melting at 125°–127° C. An analytical sample melted at 125°–126° C. after recrystallization from 1,2-dichloroethane and treatment with decolorizing carbon.

Analysis calculated for C9H9NO3S2: C, 44.43; H, 3.73; N, 5.76. Found: C, 44.67; H, 3.77; N, 5.97.

Step B: Preparation of
5-Hydroxy-2-sulfamoylbenzo[b]thiophene

Pyridine hydrochloride (50 g) was heated to 190° C. and to the melt was added 5-methoxy-2-sulfamoylbenzo[b]thiophene (12.78 g, 0.053 m). The mixture was stirred at 190° C. for 2 hours and then poured into ice and extracted with ethyl acetate (3×200 ml). The combined extract was washed with 3N HCl, dried over Na2SO4 and filtered through a pad of filter aid and charcoal. The filtrate was concentrated under reduced pressure and the residue was crystallized from nitromethane to yield 7.83 g (64%) of product melting at 197°–198.5° C. An analytical sample melted at 192.5°–193.5° C. after recrystallization from nitromethane and treatment with decolorizing carbon.

Analysis calculated for C8H7NO3S2: C, 41.91; H, 3.08; N, 6.11. Found: C, 42.08 and 42.11; H, 3.11 and 3.10; N, 6.38 and 6.12.

EXAMPLE 6

5-Acetoxy-2-sulfamoylbenzo[b]thiophene

A solution of 5-hydroxy-2-sulfamoylbenzo[b]thiophene (4.00 g, 0.017 m) in acetone (70 ml) was cooled to −5° C., triethylamine (1.92 g, 0.019 m) was added, followed by the dropwise addition of a solution of acetyl chloride (1.48 g, 0.019 m) in acetone (10 ml) over 15 minutes, maintaining the temperature at −5° to −3° C. After stirring at −5° C. for 2¼ hours, the mixture was filtered and the solid was washed with acetone. The combined filtrate and washings were concentrated under reduced pressure, the residue was dissolved in ethyl acetate (7.5 ml) washed with water (2×20 ml), dried and evaporated under reduced pressure. The residue was crystallized from 1,2-dichloroethane to yield 4.01 g (87%) of product melting at 129°–132° C. An analytical sample melted at 131.5°–133° C. after recrystallization from 1,2-dichloroethane.

Analysis calculated for C10H9NO4S2: C, 44.27; H, 3.34; N, 5.16. Found: C, 44.53; H, 3.28; N, 4.99.

Employing the procedure substantially as described in Example 6, but substituting for the acetyl chloride used therein an approximately equimolar amount of the acid chlorides or acid anhydrides described in Table II there are produced the acyloxy-2-sulfamoylbenzo[b]thiophenes also described in Table II in accordance with the following reaction scheme.

TABLE II

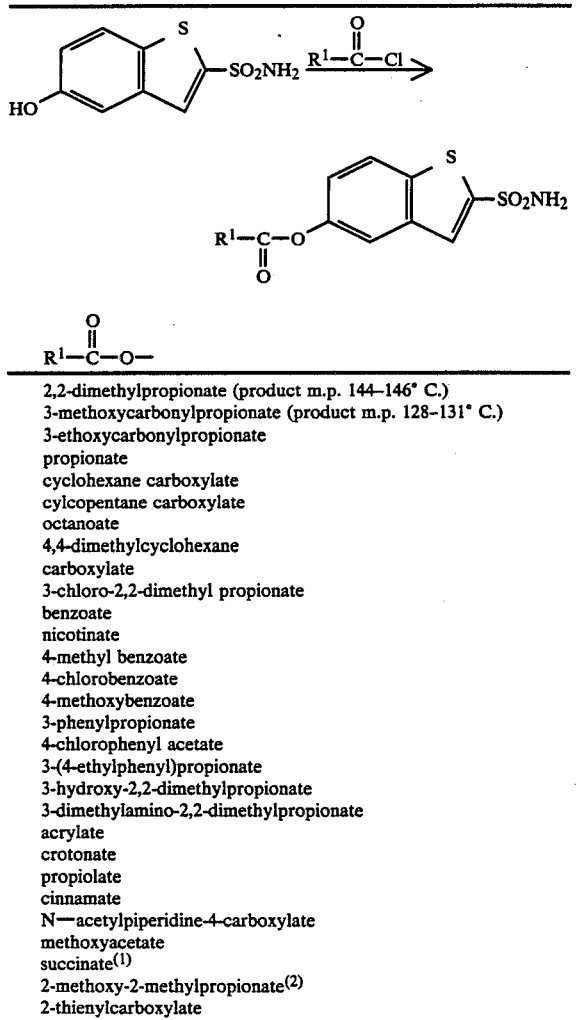

| $R^1-\overset{O}{\underset{\|}{C}}-O-$ |
|---|
| 2,2-dimethylpropionate (product m.p. 144–146° C.) |
| 3-methoxycarbonylpropionate (product m.p. 128–131° C.) |
| 3-ethoxycarbonylpropionate |
| propionate |
| cyclohexane carboxylate |
| cylcopentane carboxylate |
| octanoate |
| 4,4-dimethylcyclohexane carboxylate |
| 3-chloro-2,2-dimethyl propionate |
| benzoate |
| nicotinate |
| 4-methyl benzoate |
| 4-chlorobenzoate |
| 4-methoxybenzoate |
| 3-phenylpropionate |
| 4-chlorophenyl acetate |
| 3-(4-ethylphenyl)propionate |
| 3-hydroxy-2,2-dimethylpropionate |
| 3-dimethylamino-2,2-dimethylpropionate |
| acrylate |
| crotonate |
| propiolate |
| cinnamate |
| N—acetylpiperidine-4-carboxylate |
| methoxyacetate |
| succinate[1] |
| 2-methoxy-2-methylpropionate[2] |
| 2-thienylcarboxylate |

[1]acylating reagent is succinic anhydride
[2]acylating reagent is 2-methoxy-2-methylpropionic N,N—diphenyl carbamic anhydride

EXAMPLE 7

5-Bromo-2-sulfamoylbenzo[b]thiophene

Step A: Preparation of 4-Bromophenyl-2,2-diethoxyethylsulfide

To a solution of p-bromothiophenol (117.2 g, 0.62 mol), $K_2CO_3$ (171.4 g, 1.24 mol) in acetone (500 ml) was added dropwise under $N_2$, bromoacetaldehyde diethylacetal (90 ml, d=1.31, 0.6 mol). After stirring overnight at room temperature, the reaction mixture was filtered and the filtrate reconcentrated to dryness to provide a quantitative yield of product. The material was used directly in the next step without further purification.

Step B: Preparation of 5-Bromobenzo[b]thiophene

To a mixture of polyphosphoric acid (300 g) and chlorobenzene (300 ml) heated at 135° C. under $N_2$ was added the acetal from Step A (61 g, 0.2 mol) over 10 minutes under $N_2$. After 0.5 h, the hot mixture was poured onto ice —$H_2O$ and the resulting solution extracted 4× with $CHCl_3$. The organic extracts were washed with $H_2O$, saturated $Na_2CO_3$ solution, dried, filtered and concentrated to dryness. The residue was distilled to yield 25.5 g (60%) of product; b.p. 106° C.

Step C: Preparation 5-Bromo-2-sulfamoylbenzo[b]thiophene

Employing the procedure substantially as described in Example 1, Step C but substituting for the 6-methoxybenzo[b]thiophene used therein an equimolar amount of 5-bromobenzo[b]thiophene, there was produced the subject compound in 17% yield, m.p. 211°–213° C., after recrystallization from acetonitrile.

EXAMPLE 8

7-Methoxy-2-sulfamoylbenzo[b]thiophene

Employing the procedure substantially as described in Example 7, Steps A, B and C but substituting for the 4-bromothiophenol used in Step A thereof an equimolar amount of 2-methoxythiophenol there are produced in sequence:

7-methoxyphenyl-2,2-diethoxyethylsulfide in quantitative yield (not characterized);

7-methoxybenzo[b]thiophene in 42% yield, b.p. 0.5 mm 100°–110° C.; and 7-methoxy-2-sulfamoylbenzo[b]thiophene in 55% yield, m.p. 195°–197° C.

EXAMPLE 9

7-Hydroxy-2-sulfamoylbenzo[b]thiophene

Employing the procedure substantially as described in Example 1, Step D but substituting for the 6-methoxy-2-sulfamoylbenzo[b]thiophene used therein, an equimolecular amount of 7-methoxy-2-sulfamoylbenzo[b]thiophene, there was produced 7-hydroxy-2-sulfamoylbenzo[b]thiophene (55% yield) m.p. 196°–198° C.

Employing the procedure substantially as described in Example 6, but using as the acylating agent acetyl chloride as used therein or an approximately equimolar amount of the acid chlorides described in Table III and substituting for the 5-hydroxy-2-sulfamoylbenzo[b]thiophene used therein an equimolar amount of 7-hydroxy-2-sulfamoylbenzo[b]thiophene or 4-hydroxy-2-sulfamoylbenzo[b]thiophene there are produced the acyloxy-2-sulfamoylbenzo[b]thiophenes also described in Table III in accordance with the following reaction scheme.

TABLE III

| Position | $R^1-\overset{O}{\underset{\|}{C}}-O-$ |
|---|---|
| 7 | 2,2-dimethylpropionate |
| 7 | 3-methoxycarbonylpropionate |
| 7 | acetate |
| 4 | 2,2-dimethylpropionate |
| 4 | 3-methoxycarbonylpropionate |
| 4 | acetate |
| 7 | propionate |
| 4 | cyclohexane carboxylate |

TABLE III-continued

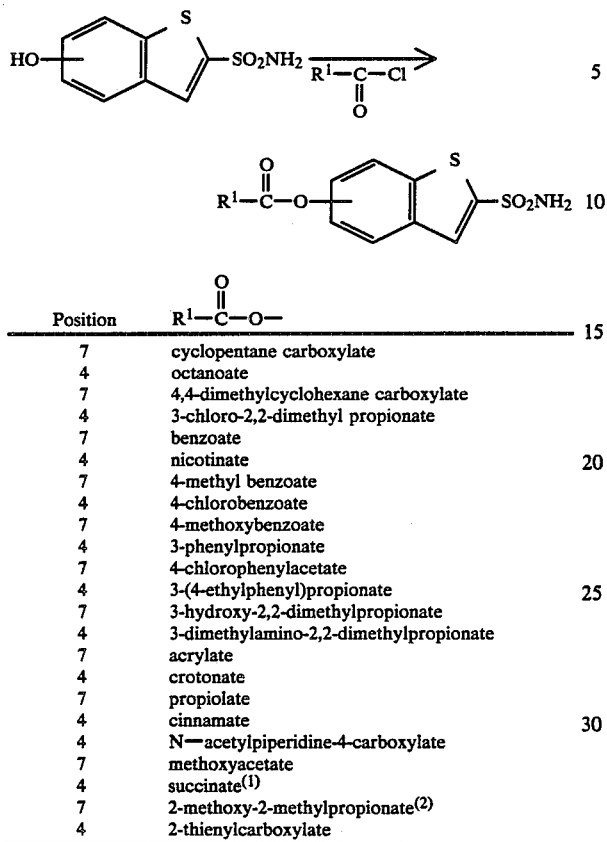

| Position | R¹—C(=O)—O— |
|---|---|
| 7 | cyclopentane carboxylate |
| 4 | octanoate |
| 7 | 4,4-dimethylcyclohexane carboxylate |
| 4 | 3-chloro-2,2-dimethyl propionate |
| 7 | benzoate |
| 4 | nicotinate |
| 7 | 4-methyl benzoate |
| 4 | 4-chlorobenzoate |
| 7 | 4-methoxybenzoate |
| 4 | 3-phenylpropionate |
| 7 | 4-chlorophenylacetate |
| 4 | 3-(4-ethylphenyl)propionate |
| 7 | 3-hydroxy-2,2-dimethylpropionate |
| 4 | 3-dimethylamino-2,2-dimethylpropionate |
| 7 | acrylate |
| 4 | crotonate |
| 7 | propiolate |
| 4 | cinnamate |
| 4 | N—acetylpiperidine-4-carboxylate |
| 7 | methoxyacetate |
| 4 | succinate[1] |
| 7 | 2-methoxy-2-methylpropionate[2] |
| 4 | 2-thienylcarboxylate |

[1] acylating reagent is succinic anhydride
[2] acylating reagent is 2-methoxy-2-methylpropionic N,N—diphenyl carbamic anhydride

EXAMPLE 10

6-(2-Sulfamoylbenzo[b]thienyl 2-Methylpropyl Carbonate

A solution of 6-hydroxy-2-sulfamoylbenzo[b]thiophene (2.5 g.; 0.01 mole) in acetone (45 ml) at −5° was treated with triethylamine (1.21 g; 0.01 mole). Then a solution of isobutyl chloroformate (1.64 g; 0.012 mole) in acetone (5 ml) was added, dropwise, during 15 min. at −5°.

After 15 minutes, the reaction mixture was poured into water (300 ml). The resulting semi-solid was extracted into ethyl acetate, washed with saturated sodium chloride solution and dried over sodium sulfate. Removal of solvent in vacuo gave a solid. The yield was 3.59 g, m.p. 109°–123° C. Recrystallization from butyl chloride gave the pure title compound m.p. 129°–130°.

Analysis calculated for $C_{13}H_{15}NO_5S_2$: C, 47.40; H, 4.59; N, 4.25. Found: C, 47.65; H, 4.76; N, 4.11.

Employing the procedure substantially as described in Example 10 but substituting for the 6-hydroxy-2-sulfamoylbenzo[b]thiophene used therein equimolecular amounts of the 4,5 or 7-hydroxy-2-sulfamoylbenzo[b]thiophenes and using isobutyl chloroformate as in Example 10 or substituting therefore the chloroformates described in Table IV, there are produced the 4,5,6 or 7 (2-sulfamoylbenzo[b]thienyl) carbonates also described in Table IV in accordance with the following reaction scheme:

TABLE IV

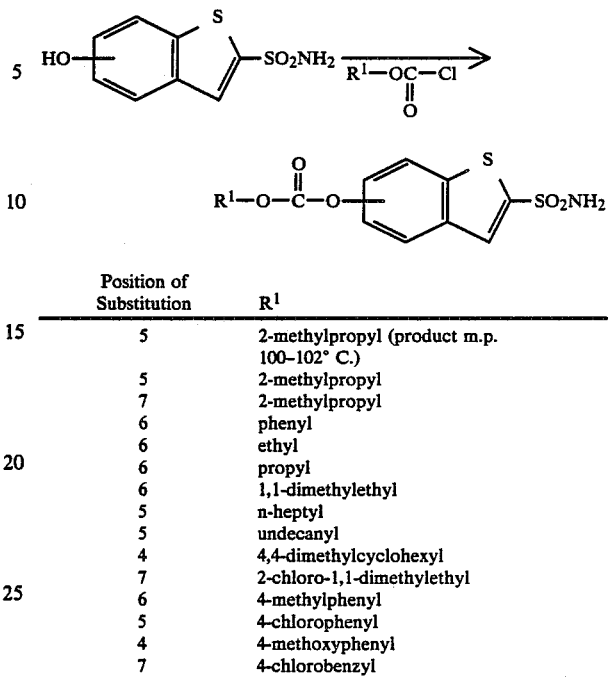

| Position of Substitution | R¹ |
|---|---|
| 5 | 2-methylpropyl (product m.p. 100–102° C.) |
| 5 | 2-methylpropyl |
| 7 | 2-methylpropyl |
| 6 | phenyl |
| 6 | ethyl |
| 6 | propyl |
| 6 | 1,1-dimethylethyl |
| 5 | n-heptyl |
| 5 | undecanyl |
| 4 | 4,4-dimethylcyclohexyl |
| 7 | 2-chloro-1,1-dimethylethyl |
| 6 | 4-methylphenyl |
| 5 | 4-chlorophenyl |
| 4 | 4-methoxyphenyl |
| 7 | 4-chlorobenzyl |

EXAMPLE 11

(S)-6-[3-(1,1-Dimethylethyl)oxazolidin-2-on-5-yl]methoxy-2-sulfamoylbenzo[b]thiophene Step A: Preparation of N,N-Dimethyl-N'-(6-hydroxy-2-sulfamoylbenzo[b]thiophene)formamidine To a partial suspension of 6-hydroxy-2-sulfamoylbenzo[b]thiophene (2.29 g, 10 mmol) in acetonitrile (10 ml) under a nitrogen atmosphere was added dropwise a solution of N,N-dimethylformamide dimethyl acetal (1.6 ml, 12 mmol) in acetonitrile (10 ml). After ½ hour, water was added and the product was extracted into ethyl acetate, dried ($Na_2SO_4$) and evaporated to dryness. The residue was crystallized from hot 1,2-dichloroethane, after treatment with charcoal, to give 2.1 g of product, m.p. 164°–166° C.

Step B: Preparation of (S)-N,N-Dimethyl-N'-[[3-(1,1-dimethylethyl)oxazolidin-2-on-5-yl]methoxy-2-sulfamoylbenzo[b]thiophene]-formamidine A solution of (S)-3-(1,1-dimethylethyl)-5-(hydroxymethyl)oxazolidinone mesylate (4.26 g, 17 mmol) in DMSO (15 ml) was added dropwise to a solution of N,N-dimethyl-N'-(6-hydroxy-2-sulfamoylbenzo[b]thiophene)formamidine (4.26 g, 15 mmol) in DMSO (15 ml) containing potassium carbonate (2.8 g, 20 mmol) warmed at 70° C. under a nitrogen atmosphere and stirring was continued at 70° C. for 20–24 hours. The reaction mixture was poured into ice water and extracted with ethyl acetate/acetonitrile, dried ($Na_2SO_4$) and concentrated to a small volume. The crystalline product was collected (wt.; 5.5 g) and recrystallized twice from ethyl acetate, m.p. 121°–25° C.

Anal. calcd. for $C_{19}H_{25}N_3O_5S_2$: N, 9.56; C, 51.92; H, 5.73. Found: N, 9.58; C, 51.55; H, 5.76.

Step C: Preparation of (S)-6-[3-(1,1-Dimethylethyl)oxazolidin-2-on-5-yl]methoxy-2-sulfamoylbenzo[b]thiophene A suspension of the product from Step B (5.4 g, 14.5 mmol) was heated at 100° C. in 6N HCl (75 ml) for 3–4 hours, cooled with ice and extracted with ethyl acetate, dried ($Na_2SO_4$) and evaporated to give 5.8 g of crude product. The mixture was dissolved in hot 1,2-dichloroethane, filtered hot to remove dealkylated product (1.3 g) and evaporated. The residue (4.5 g) was chromatographed on silica gel eluting with a gradient of 1.5–6% methanol/chloroform (v/v). The purified product was recrystallized from 1,2-dichloroethane to give 3.2 g of product, m.p. 147°–149° C.

Anal. calcd. for $C_{16}H_{20}N_2O_5S_2$: N, 7.29; C, 49.98; H, 5.24. Found: N, 7.36; C, 50.09; H, 5.37.

Employing the procedure of Example 11, Steps A, B and C but using 4,5- or 7-hydroxy-2-sulfamoylbenzo[b]thiophene in place of the 6-hydroxy analog, there are produced the (S)-4,5- or 7-[3-(1,1-dimethylethyl)oxazolidin-2-on-5-yl]methoxy-2-sulfamoylbenzo[b]thiophenes respectively.

EXAMPLE 12

(S)-6-[(Oxazolidin-2-on-5-yl)methoxy]-2-sulfamoylbenzo[b]thiophene

Crude by-product (1.3 gm) isolated from Step C of Example 11 was dissolved in hot ethyl acetate/acetonitrile, treated with charcoal, and the solvents were boiled off until crystallization began. Collected 0.83 gm, m.p. 198°–199° C.

Anal. calcd. for $C_{12}H_{12}N_2O_5S_2$: N, 8.53; C, 43.89; H, 3.68. Found: N, 8.58; C, 44.04; H, 3.63.

Similarly prepared are the (S)-4,5 or 7-[(oxazolidin-2-on-5-yl)methoxy]-2-sulfamoylbenzo[b]thiophene.

EXAMPLE 13

(S)-6-[3-(1,1-Dimethylethylamino)-2-hydroxy-propoxy-2-sulfamoylbenzo[b]thiophene Hydrochloride A suspension of (S)-6-[3-(1,1,-dimethylethyl)oxazolidin-2-on-5-yl]methoxy-2-sulfamoylbenzo[b]thiophene (2.47 g, 6.4 mmol) in a solution of water/ethanol (2:1 (v/v), 20 ml) containing 40% NaOH (w/v) (5 ml) was heated at 100° C. for 3 days. THe reaction mixture was cooled, acidified with hydrochloric acid, filtered to remove insoluble material and evaporated to dryness. The residue was repeatedly extracted with hot ethanol, filtered and the ethanol extracts evaporated. The resultant residue was triturated with ethanol/diethyl ether to give a solid product (wt. 1.95 g). After several recrystallizations which involved dissolution of the solid in hot methanol, followed by addition of ethanol, and boiling off solvents until crystallization began, there was obtained 1.2 g of product, m.p. 266°–268° C.

Anal. calcd. for $C_{15}H_{22}N_2O_4S_2.HCl.0.4NaCl.0.4H_2O$: C, 42.37; N, 6.59; H, 5.57; Cl, 11.67. Found: C, 42.33; N, 6.62; H, 5.57; Cl, 11.42.

Similarly prepared are the (S)-4,5 or 7-[3-(1,1-dimethylethylamino)-2-hydroxypropoxy]-2-sulfamoylbenzo[b]thiophene.

EXAMPLE 14

6-(2-Ketopropoxy)-2-sulfamoylbenzo[b]thiophene

Step A: Preparation of N,N-Dimethyl-N'-[6-(2-ketopropoxy)-2-sulfamoylbenzo[b]thiophene formamidine Chloroacetone (1.2 ml) was added dropwise to a stirred mixture of anhydrous potassium carbonate (2.0 g) and N,N-dimethyl-N'-[6-hydroxy-2-sulfamoylbenzo[b]thiophene]formamidine (2.90 g) in dimethylsulfoxide (20 ml) at 25° C. After 24 hours, the reaction mixture was diluted with water (200 ml) and the solid that formed was collected and dried, 3.02 g, m.p. 150°–153° C.

Step B: Preparation of 6-(2-Ketopropoxy)-2-sulfamoylbenzo[b]thiophene

The product from Step A was heated to reflux with a mixture of methanol (50 ml) and 6N hydrochloric acid (50 ml) for 0.5 hour. The cooled solution was diluted with water (300 ml) and chilled. The precipitated solid was collected, washed with water and dried, to give 2.25 g, m.p. 181°–185° C. Recrystallization from acetonitrile gave a sample with m.p. 184°–187°.

Anal. calcd. for $C_{11}H_{11}NO_4S_2$: C, 46.30; H, 3.89; N, 4.91. Found: C, 46.48; H, 3.87; N, 5.02.

Similarly prepared are the 4,5 or 7-(2-ketopropoxy)-2-sulfamoylbenzo[b]thiophenes.

EXAMPLE 15

6-[(Ethoxycarbonyl)methoxy]-2-sulfamoylbenzo[b]thiophene

To a solution of ethyl bromoacetate (1.2 ml, 11 mmol) and 6-hydroxy-2-sulfamoylbenzo[b]thiophene (2.29 g, 10 mmol) in DMSO (10 ml) was added dropwise a solution of potassium bicarbonate (1.0 g, 10 mmol) and potassium carbonate (0.13 g, 1 mmol) in water (7 ml). The mixture was stirred for 1–2 days, then diluted with water. The precipitated product was collected dissolved in ethyl acetate, dried ($Na_2SO_4$) and evaporated to dryness. The residue was recrystallized from hot ethyl acetate, boiling off solvent until crystallization began, to give 1.2 g of product, m.p. 182°–184° C.

Anal. calcd. for $C_{12}H_{13}NO_5S_2$: C, 45.70; H, 4.15; N, 4.44. Found: C, 46.11; H, 4.32; N, 4.39.

Following the procedure of Example 15, there are also produced 4,5 or 7-[(ethoxycarbonyl)methoxy]-2-sulfamoylbenzo[b]thiophene. The 5-isomer has m.p. 167.5°–168° C.

EXAMPLE 16

6-[(Carboxy)methoxy]-2-sulfamoylbenzo[b]thiophene

Solid 6-[(ethoxycarbonyl)methoxy]-2-sulfamoylbenzo[b]thiophene (1.6 g, 5 mmol) was added to 10% NaOH (40 ml) and stirred at room temperature 4–6 hours. The solution was acidified and extracted with ethyl acetate, dried ($Na_2SO_4$) and evaporated. The residue was dissolved in hot ethyl acetate, filtered, and evaporated until crystallization began to give 0.94 g of product, m.p. 205°–208°.

Anal. calcd. for $C_{10}H_9NO_5S_2$: N, 4.88; C, 41.80; H, 3.16. Found: N, 4.92; C, 42.07; H, 3.24.

By similar procedures there are prepared the 4,5 or 7-[(carboxy)methoxy]-2-sulfamoylbenzo[b]thiophene.

EXAMPLE 17

6-[3-Carboxypropoxy]-2-sulfamoylbenzo[b]thiophene

Step A: Preparation of N,N-Dimethyl-N'-[6-(3-(ethoxycarbonyl)propoxy)-2-sulfamoylbenzo[b]thiophene formamidine Ethyl-4-bromobutyrate (2.15 g, 11.0 mmol) was added dropwise to a stirred solution of N,N-dimethyl-N'-[6-hydroxy-2-sulfamoylbenzo[b]thiophene formamidine (2.84 g, 10.0 mmol) and potassium carbonate (2.07 g, 15.0 mmol) in dimethyl sulfoxide (20.0 ml). The reaction temperature was kept at 70° C. for 18 hours. The reaction mixture was cooled, poured into water (100 ml) and extracted with ethyl acetate (3×150 ml). The combined ethyl acetate extracts were washed with water (3×50 ml), brine (2×25 ml) and dried ($Na_2SO_4$). The ethyl acetate was removed under vacuum to yield an oil (2.85 gm).

Step B: Preparation of 6-(3-carboxypropoxy)-2-sulfamoylbenzo[b]thiophene

N,N-Dimethyl-N'-[6-(3-(ethoxycarbonyl)propoxy)-2-sulfamoylbenzo[b]thiophene]formamidine (2.85 g, 7.2 mmol) was suspended in hydrochloric acid (25.0 ml, 6.0N) and warmed to 70° C. for 6 hours. The reaction was cooled and the solid which formed collected via vacuum filtration. The solid was dissolved in ethyl acetate-methanol (160 ml, 3 to 1 (v/v)) and filtered through charcoal. The solvent was removed under vacuum and the remaining solid dried under vacuum to yield a white solid (2.0 g, 6.3 mmol), m.p. 186°–187° C.

Anal. calcd.: C, 45.70; H, 4.15; N, 4.44. Found: C, 45.78; C, 4.14; N, 4.31.

Similarly prepared are the 4,5 or 7-(3-carboxypropoxy)-2-sulfamoylbenzo[b]thiophenes.

EXAMPLE 18

6-[2,3-Epoxypropoxy]-2-sulfamoylbenzo[b]thiophene

Step A: Preparation of 6-allyloxy-2-sulfamoylbenzo[b]thiophene

Allyl bromide (2.07 ml, 24.0 mmol) was added dropwise to a stirred solution of 6-hydroxy-2-sulfamoylbenzo[b]thiophene (5.0 g, 22.0 mmol) in dimethylsulfoxide (15.0 ml). A solution of $K_2CO_3$ (3.34 g, 24.0 mmol) in water (7.5 ml) was added dropwise to the reaction solution at 25° C. After 24 hours, the reaction mixture was diluted with water (50 ml). The solid that formed was collected and dried, 3.75 gm (13.9 mmol), m.p. 101°–102° C.

Step B: Preparation of 6-[3(2)-hydroxy-2(3)-bromopropoxy]-2-sulfamoylbenzo[b]thiophene 6-[Allyloxy]-2-sulfamoylbenzo[b]thiophene (5.0 gm, 18.6 mmol) was added to a solution of water (5.0 ml) in DMSO (30 ml) with stirring. The solution was cooled to 0° C. and N-bromosuccinimide (3.5 g, 19.5 mmol) was added. The reaction mixture was allowed to warm to room temperature and after 2.0 hours was poured into water (150 g). The aqueous mixture was extracted with ethyl acetate (3×100 ml) and the combined extracts washed with water (2×25 ml), brine (2×25 ml) and dried ($Na_2SO_4$). The ethyl acetate was removed under vacuum to give a red oil (5.5 g, 15.0 mmol).

Step C: Preparation of 6-[2,3-epoxypropoxy]-2-sulfamoylbenzo[b]thiophene

6-[3(2)-Hydroxy-2(3)-bromopropoxy]-2-sulfamoylbenzo[b]thiophene (11.1 g, 30.2 mmol) was dissolved in methanol (25 ml). A solution of potassium hydroxide (3.9 g), 60.4 mm) in methanol (20 ml) was added dropwise. After 2.5 hours, the reaction mixture was poured into water (100 ml). The mixture was acidified with concentrated hydrochloric acid. The aqueous mixture was extracted with ethyl acetate (3×100 ml) and the combined ethyl acetate extracts washed with water (2×100 ml), brine (2×100 ml) and dried ($Na_2SO_4$). The ether was removed under vacuum. The solid which remained was purified using medium pressure chromatography (55% hexane/45% ethyl acetate, v/v), m.p. 148°–149° C.

Anal. calcd.: $C_{11}H_{11}NO_4S_2$: C, 46.30; H, 3.89; N, 4.91. Found: C, 46.43; C, 3.90; N, 4.93.

Using the procedures of Example 18, there are also prepared the 4,5 or 7-(2,3-epoxypropoxy)-2-sulfamoylbenzo[b]thiophenes.

EXAMPLE 19

6-[3-Methoxy-2-hydroxypropoxy]-2-sulfamoylbenzo[b]thiophene

One drop of concentrated sulfuric acid was added to a solution of 6-[2,3-epoxypropoxy]-2-sulfamoylbenzo[b]thiophene (2.0 g, 7.0 mmol) in methanol (25 ml). After 18 hours, the methanol was removed under vacuum. The residue was dissolved in ethyl acetate (200 ml), washed with water (2×25 ml), brine (2×25 ml) and dried ($Na_2SO_4$). The ethyl acetate was removed under vacuum. The white solid remaining was recrystallized from boiling ethyl acetate, 1.5 g, m.p. 128°–129° C.

Anal. calcd.: $C_{12}H_{15}NO_5S_2$: C, 45.41; H, 4.76; N, 4.41. Found: C, 45.38; C, 4.76; N, 4.60.

Similarly prepared are the 4,5 or 7-(3-methoxy-2-hydroxypropoxy)-2-sulfamoylbenzo[b]thiophenes.

EXAMPLE 20

6-(2,3-Dihydroxypropoxy)-2-sulfamoylbenzo[b]thiophene

Step A: Preparation of N,N-Dimethyl-N'-[[6-(2,2-dimethyl-1,3-dioxolan-3-yl)methoxy]-2-sulfamoylbenzo[b]thiophene]formamidine N,N-dimethyl-N'-[6-hydroxy-2-sulfamoylbenzo[b]thiophene]formamidine (5.0 g, 17.6 mmol) was added to a mixture of $K_2CO_3$ (3.64 g, 26.4 mmol) in DMSO (25 ml). 2,2-Dimethyl-1,3-dioxolane-4-methanol (4.07 g, 19.3 mmol) was added to the reaction dropwise. The reaction temperature was kept at 70° C. for 18 hours. The cooled reaction was poured into water (100 ml) and extracted with ethyl acetate containing a small amount of methanol (4×25 ml). The combined ethyl acetate extracts were washed with water (4×25 ml), brine (2×25 ml) and dried ($MgSO_4$). The ethyl acetate was removed under vacuum to yield a tan solid (6.0 g).

Step B: 6-(2,3-Dihydroxypropoxy)-2-sulfamoylbenzo[b]thiophene

N,N-dimethyl-N'-[[6-(2,2-dimethyl-1,3-dioxolan-3-yl)-methoxy]-2-sulfamoylbenzo[b]thiophene]formamidine (6.0 g, 15.0 mmol) was added to 6.0N HCl (25 ml) and the mixture warmed to 70° C. for 18 hours. The cooled reaction was extracted with ethyl acetate (4×150 ml) and the combined extracts washed with water (1×50 ml), brine (2×50 ml) and dried (MgSO4). The ethyl acetate was removed under vacuum to yield a white solid. Recrystallization from nitromethane gave 4.0 g, m.p. 134°–135° C.

Anal. calcd.: $C_{11}H_{13}NO_5S_2$: C, 43.56; H, 4.32; N, 4.62. Found: C, 43.98; C, 4.31; N, 4.31.

Similarly prepared is the 4,5 or 7-(2,3-dihydroxypropoxy)-2-sulfamoylbenzo[b]thiophene.

EXAMPLE 21

5-(2,3-Dihydroxypropoxy)-2-sulfamoylbenzo[b]thiophene

Step A:
N,N-Dimethyl-N'-(5-hydroxy-2-sulfamoylbenzo[b]thiophene

A suspension of 5-hydroxy-2-sulfamoylbenzo[b]thiophene (10.65 g, 0.046 m) in acetonitrile (100 ml) was stirred while dimethylformamide dimethyl acetal (5.95 g, 0.050 m) was added quickly. After stirring at ambient temperature for 30 minutes, the mixture was added to water (200 ml) and the solid was collected and dried at 80° C. under vacuum to yield 11.39 g (87%) of product melting at 208°–209° C. An analytical sample melts at 208.5°–210° C. after recrystallization from methanol.

Anal. calcd.: $C_{11}H_{12}N_2O_3S_2$: C, 46.46; H, 4.26; N, 9.85. Found: C, 46.67; C, 4.37; N, 10.12.

Step B: Preparation of 5-(2,3-Dihydroxypropoxy)-2-sulfamoylbenzo[b]thiophene

A suspension of sodium hydride (0.21 g, 0.0044 mol, 50% dispersion in mineral oil) in dry dimethylformamide (10 ml) was stirred under nitrogen at 70° C. while N,N-dimethyl-N'-(5-hydroxy-2-sulfamoylbenzo[b]thiophene)formamidine (1.00 g, 0.0035 mol) was added portionwise over 15 minutes. After stirring at 70° C. for 30 minutes, 2,2-dimethyl-4-hydroxymethyl-1,3-dioxolane methanesulfonate (0.74 g, 0.0035 mol) was added rapidly and the mixture was heated at 70° C. for 19.5 hours. An additional 0.01 g of 50% sodium hydride and 0.19 g of 2,2-dimethyl-4-hydroxymethyl-1,3-dioxolane methanesulfonate was added and heating at 70° C. was continued for 3 hours more. The reaction mixture was poured into water (100 ml) and extracted with ethyl acetate (3×100 ml), the combined extracts were washed with water, dried over Na2SO4 and evaporated under reduced pressure. The residue was heated and stirred in 6N HCl (20 ml) for 17.5 hours. The reaction mixture was diluted with water (75 ml) and extracted with ethyl acetate (3×100 ml). After washing with water and drying over Na2SO4, the solvent was evaporated under reduced pressure to yield 0.60 g (57%) of product which was crystallized from methanol-chloroform. An analytical sample melted at 162.5°–163.5° C. after recrystallization from methanol-chloroform and treatment with decolorizing carbon.

Anal. calcd.: $C_{11}H_{13}NO_5S_2$: C, 43.55; H, 4.32; N, 4.62. Found: C, 43.22; C, 4.29; N, 4.69.

Employing the procedures substantially as described in Examples 11, 14, 15, 17, 18 or 21, there are produced the ethers of 4,5,6 or 7-hydroxy-2-sulfamoylbenzo[b]thiophene described in Table V in accordance with the following reaction scheme:

TABLE V

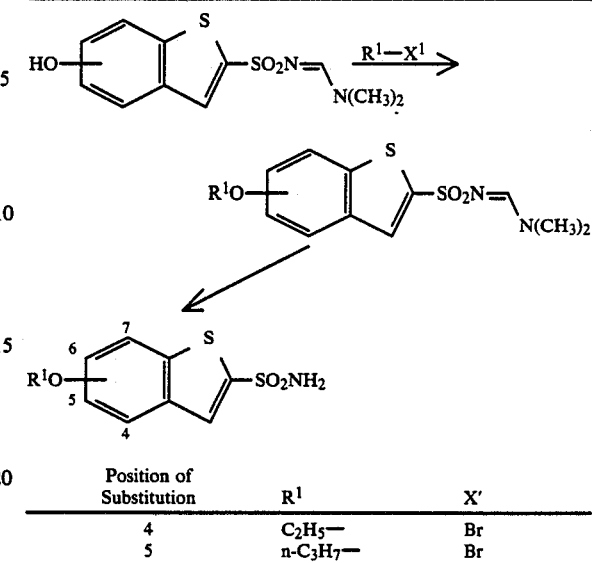

| Position of Substitution | $R^1$ | X' |
|---|---|---|
| 4 | $C_2H_5$— | Br |
| 5 | n-$C_3H_7$— | Br |

EXAMPLE 22

5-(Dibenzyl)amino-2-sulfamoylbenzo[b]thiophene

Step A: Preparation of 5-Dibenzylaminobenzo[b]thiophene

A stirred solution of 5-aminobenzo[b]thiophene hydrochloride (4.65 g, 0.025 mole) in dry DMSO (40 ml) was treated with benzyl bromide (6 ml, 0.05 mole) followed by solid NaHCO3 (6.3 g, 0.075 mole). After the immediate, vigorous evolution of CO2, the mixture set to a solid mass. This was held at ambient temperature overnight and the solid then was collected and recrystallized from CH3CN to obtain 5.0 g (61%) of 5-(dibenzyl)aminobenzo[b]thiophene, m.p. 114°–117° C. A sample recrystallized from ethyl acetate-hexane melted at 115°–117° C.

Anal. calcd.: $C_{22}H_{19}NS$: C, 80.20; H, 5.81; N, 4.25. Found: C, 80.49; H, 5.86; N, 3.90.

Step B: Preparation of 5-(Dibenzyl)amino-2-sulfamoylbenzo[b]thiophene

The subject compound was prepared by the procedure described in Example 1, Step C, using 5-dibenzylaminobenzo[b]thiophene in place of 6-methoxybenzo[b]thiophene. The crude product was recrystallized from 1,2-dichloroethane-hexane and then from 70% ethanol to obtain 52% of 5-(dibenzyl)amino-2-sulfamoylbenzo[b]thiophene as a light tan solid, m.p. 122°–124° C.

Anal. calcd.: $C_{22}H_{20}N_2O_2S_2$: C, 64.68; H, 4.93; N, 6.86. Found: C, 64.82; H, 4.95; N, 7.11.

EXAMPLE 23

5-(Dimethyl)amino-2-sulfamoylbenzo[b]thiophene

Step A: Preparation of 5-(Dimethyl)aminobenzo[b]thiophene

To a stirred solution of 5-aminobenzo[b]thiophene (4.55 g, 0.03 mole) in CH3CN (175 ml) was added 37% aqueous formaldehyde (28 ml, 0.035 mole) followed by sodium cyanoborohydride (6.65 g, 0.105 mole). Glacial acetic acid (3.5 ml) was added in small increments over 15 minutes. After 1 hour, another 3.5 ml of acetic acid was added and after another 1 hour, the mixture was poured into ether (700 ml). The ethereal layer was separated, washed with 1M KOH (3×) then with saturated NaCl solution, dried over anhydrous Na$_2$SO$_4$, and evaporated to dryness in vacuo. The residual dark oily solid was purified by chromatography on 800 ml of silica gel. Elution with 97 hexane: 3 ethyl acetate afforded 4.6 g (88%) of 5-(dimethyl)aminobenzo[b]thiophene as a light yellow solid, m.p. 52°–54° C.

Anal. calcd.: C$_{10}$H$_{11}$NS: C, 67.75; H, 6.26; N, 7.90. Found: C, 67.12; H, 6.24; N, 7.85.

Step B: Preparation of
5-(Dimethyl)amino-2-sulfamoylbenzo[b]thiophene

The subject compound was prepared by the procedure described in Example 1, Step C, using 5-(dimethyl)aminobenzo[b]thiophene in place of 6-methoxybenzo[b]thiophene. The crude product was obtained in 60% yield as a dark yellow solid. Two recrystallizations from 1,2-dichloroethane, decolorizing with charcoal afforded 5-(dimethyl)amino-2-sulfamoylbenzo[b]thiophene as light yellow needles, m.p. 197°–199° C.

Anal. calcd.: C$_{10}$H$_{12}$N$_2$O$_2$S$_2$: C, 46.85; H, 4.72; N, 10.93. Found: C, 47.17; H, 4.52; N, 10.56.

EXAMPLE 24

4-Chloro-5-morpholino-2-sulfamoylbenzo[b]thiophene and 5-Morpholino-2-sulfamoylbenzo[b]thiophene Step A: Preparation of 5-Morpholinobenzo[b]thiophene 5-Aminobenzo[b]thiophene (5.4 g, 0.0362 mole), bis-(2-chloroethyl)ether (5.2 g, 0.0364 mole) and 40% aqueous NaOH (0.073 mole) were stirred vigorously and heated to refluxing for 22 hours. The cooled mixture was extracted with CHCl$_3$. Evaporation of the washed and dried CHCl$_3$ extract under reduced pressure left 7.0 g (88%) of the crude product as a slightly oily, dark yellow solid. This material was combined with 1.75 g of comparable crude product from a previous run. Recrystallization from CH$_3$CN afforded 5.50 g of 5-morpholinobenzo[b]thiophene, m.p. 127°–132° C., that was characterized by nmr.

Step B: Preparation of
4-chloro-5-morpholinobenzo[b]thiophene-2-sulfonamide and
5-Morpholinobenzo[b]thiophene-2-sulfonamide Under N$_2$, a solution of 5-morpholinobenzo[b]thiophene (4.0 g, 0.0182 mole) in dry, peroxide-free THF (35 ml) was stirred and cooled to −20° C. n-Butyllithium (12.5 ml of a 1.6M solution in hexane) was added dropwise over 10–15 min. The resulting red solution was stirred at −20° C. for 30 minutes and then SO$_2$ was passed over the surface for 30 minutes. After the thick suspension was stirred at ambient temperature for 1.25 hours, it was poured into ether and the solid lithium sulfinate derivative was collected and washed with ether. This solid was suspended in dry CH$_2$Cl$_2$ (60 ml) and cooled to 5°–10° C. N-chlorosuccinimide (3.15 g, 0.0236 mole) was added in portions over 10 min. After another 30 minutes of stirring in the cold, the mixture was filtered and the solvent was stripped from the filtrate in vacuo. The residual dark red, oily sulfonyl chloride (6.55 g) was dissolved in acetone (50 ml) and added to a stirred mixture of conc. NH$_4$OH (35 ml) and acetone (35 ml). After 45 minutes, the mixture was concentrated in vacuo and the oily product was extracted into ethylacetate. Evaporation of the washed and dried ethyl acetate extract under reduced pressure left 5.4 g of the crude mixed sulfonamides as a brown foam. This material was combined with 1.1 g of comparable crude product from a previous run and chromatographed on 500 g of silica gel, eluting with ethyl acetate-hexane (1:1).

Chromatographic fractions containing the less polar component were pooled and concentrated to yield 1.15 g (19%) of 4-chloro-5-morpholino-2-sulfamoylbenzo[b]thiophene, m.p. 195°–199° C. Recrystallization from CH$_3$CN gave 600 mg, m.p. 201°–203° C.

Analysis calculated for C$_{12}$H$_{13}$ClN$_2$O$_3$S$_2$: C, 43.30; H, 3.94; N, 8.42. Found: C, 43.57; H, 3.87; N, 8.06.

Chromatographic fractions containing the more polar component were pooled and concentrated to yield 4.0 g (74%) of 5-morpholino-2-sulfamoylbenzo[b]thiophene. Recrystallization from ethyl acetate gave 3.4 g, m.p. 155°–156° C.

Analysis calculated for C$_{12}$H$_{14}$N$_2$O$_3$S$_2$: C, 48.30; H, 4.73; N, 9.39. Found: C, 48.59; H, 4.81; N, 9.57.

EXAMPLE 25

5-Methyl-2-sulfamoylbenzo[b]thiophene

5-Methyl-2-sulfamoylbenzo[b]thiophene was prepared from 5-methylbenzo[b]thiophene (8.85 g, 0.06 mol) using the procedure for the preparation of Example 1, Step C. Yield of product was 9.8 g (72%), m.p. 212°–213° C.

EXAMPLE 26

5-Methoxymethyl-2-sulfamoylbenzo[b]thiophene

Step A: Preparation of
5-Methoxymethylbenzo[b]thiophene

To a stirred mixture of powdered KOH (18.9 g, 0.336 mol) in dimethylsulfoxide (100 ml) was added 5-hydroxymethylbenzo[b]thiophene (13.8 g, 0.084 mol) in 25 ml of dimethylsulfoxide. Then methyl iodide (23.9 g, 0.168 mol) was added dropwise at ambient temperature over several minutes. Stirring was continued for 1½ hours. The mixture was filtered, diluted with water (150 ml) and extracted with methylene chloride (200 ml) in three portions. The combined extracts were washed with water, dried over anhydrous Na$_2$SO$_4$, filtered and concentrated in vacuo. This gave 14.1 g of amber liquid. Distillation gave 10.47 g of colorless liquid, b.p. 2.2 mm Hg 110°–111° C. (Yield 70%).

Step B: Preparation of
5-Methoxymethyl-2-sulfamoylbenzo[b]thiophene

5-Methoxymethyl-2-sulfamoylbenzo[b]thiophene was prepared from 5-methoxymethylbenzo[b]thiophene (10.47 g, 0.059 mol) following the procedure for the preparation described in Example 1, Step C. Yield of product was 13.9 g (90%). M.p. (recrystallized from 1,2-dichloroethane), 124.5°–125.5° C.

EXAMPLE 27

5-Bromomethyl-2-sulfamoylbenzo[b]thiophene

To a suspension of 5-methoxymethyl-2-sulfamoylbenzo[b]thiophene, (7.4 g, 0.029 mol) in 300 ml of dry methylene chloride cooled to −30° C. was added boron tribromide (30 ml of a 1M solution in methylene chloride, 0.03 mol) over a 20 minute period. The resulting solution was stirred for 1½ hours as the temperature rose to ambient. The solution was cooled to 0° C. and there was added dropwise 150 ml of water keeping the temperature below 20° C. The methylene chloride layer was separated and the aqueous suspension was extracted with three portions (200 ml) of methanol-chloroform (50/50). The combined extracts were washed with ice water, dried over anhydrous $Na_2SO_4$, filtered and concentrated in vacuo to give 8.8 g of tan solid (quantitative yield of crude product) which after recrystallization from 1,2-dichloroethane had m.p. 171°-173° C.

EXAMPLE 28

5-Dimethylaminomethyl-2-sulfamoylbenzo[b]thiophene

To an ice cold, stirred solution of 5-bromomethyl-2-sulfamoylbenzo[b]thiophene (2.0 g, 6.5 mmol) in 25 ml of methanol was bubbled in an excess of anhydrous dimethylamine. The flask was sealed and the mixture was stirred at room temperature for 1 hour. The methanol wa removed in vacuo. The solid residue was taken up in chloroform (100 ml) and saturated $NaHCO_3$ solution (30 ml). The chloroform layer was separated and the aqueous mixture was extracted with chloroform-methanol (1/1, V/V) (50 ml). This extract was combined with the chloroform, dried over anhydrous $Na_2SO_4$, filtered and concentrated in vacuo. A solid (1.57 g) was obtained (yield 90%) which after recrystallization from nitromethane had m.p. 172°-174.5° C.

EXAMPLE 29

5-(4-Morpholinylmethyl)-2-sulfamoylbenzo[b]thiophene

To a stirred solution of morpholine (0.91 g, 10.5 mmol) and triethylamine (1.01 g, 10 mmol) in 20 ml of methanol was added 5-bromomethyl-2-sulfamoylbenzo[b]thiophene (3.06 g, 10 mmol) portionwise over 5 minutes at ambient temperature. Stirring was continued for 1¼ hours. The resulting suspension was cooled and filtered after an additional 1 hour to give 2.76 g. of yellow solid. Concentration of the filtrate in vacuo followed by trituration of the residue with water and filtering gave an additional 0.3 g of yellow solid. (Total crude yield was 98%). Recrystallization from nitromethane gave material with m.p. 221.5°-224° C.

The hydrochloride salt was also prepared using ethanolic-HCl, m.p. 244°-245° C., dec.

EXAMPLE 30

5-Acetoxymethyl-2-sulfamoylbenzo[b]thiophene

To a mixture of 5-bromomethyl-2-sulfamoylbenzo[b]thiophene (3.06, 0.01 mol), anhydrous sodium acetate (0.98 g, 0.01 mol) and glacial acetic acid (15 ml) was added three drops of triethylamine. The mixture was heated and the resulting solution was stirred at reflux for 6 hours and was left at room temperature over night. The acetic acid was removed in vacuo and the residual gum was diluted with 25 ml of ice water. The product was extracted into 3×50 ml of ether. The combined extracts were washed with water, dried over anhydrous $Na_2SO_4$, filtered and concentrated in vacuo to give 2.5 g of yellow solid (88% yield). Recrystallization from chloroform gave material with a m.p. 113°-115° C.

EXAMPLE 31

5-Hydroxymethyl-2-sulfamoylbenzo[b]thiophene

A solution of 5-acetoxymethyl-2-sulfamoylbenzo[b]thiophene (5.6 g, 19.6 mmol) in 25 ml of 1M aqueous KOH and 25 ml of methanol was stirred at room temperature for 2 hours and at reflux for 2½ hours. The mixture was filtered and the methanol was removed in vacuo. The remaining aqueous suspension was acidified with excess 6N HCl and the solid was filtered, washed with ice water and dried. The crude material (3.1 g) was chromatographed on silica gel using 5% (V/V) methanol in chloroform. Product was obtained as a yellow solid (1.85 g), m.p. 174°-176° C. Yield 41%.

EXAMPLE 32

5-(2-methoxyethyl)-2-sulfamoylbenzo[b]thiophene

Step A: Preparation of 5-(2-hydroxyethyl)benzo[b]thiophene

To a flame dried flask under $N_2$ was added magnesium turnings (6 g, 0.25 mol) and THF (100 ml). The mixture was heated at reflux and a solution of methyl iodide (7.2 ml, d=2.28, 0.116 mol), and 5-bromobenzo[b]thiophene (24.4 g, 0.114 mol) in THF (50 ml) were added dropwise. The mixture was heated at reflux for 5 hours, then cooled to 0°-4° C. and a solution of ethylene oxide (15 g, 0.33 mol) in THF (20 ml) was added dropwise. After the addition, the reaction mixture was allowed to stir at room temperature overnight. The suspension was then cooled and a solution of 3N HCl (75 ml) was added dropwise. The aqueous layer was extracted with ethyl acetate (3×) and the organic layer was backwashed with saturated $Na_2CO_3$, dried, filtered and concentrated to dryness. The residue was chromatographed on silica gel and the product was eluted with 30% ethyl acetate/hexane to yield 9.3 g (48%) of product, m.p. 56°-57° C.

Step B: Preparation of 5-(2-(methoxyethyl)benzo[b]thiophene

A suspension of KOH (6.5 g, 0.116 mol) in DMSO (55 ml) was stirred at room temperature for 5 minutes and 5-(2-hydroxyethyl)benzo[b]thiophene (5 g, 0.028 g) was added. To the above mixture, methyl iodide (3.5 ml, d=2.28, 0.056 mol) was added. After 1 hour the mixture was poured into $H_2O$ and the aqueous layer was extracted with $CH_2Cl_2$ (3×). The organic extract was washed with $H_2O$ (3×), dried, filtered and concentrated to dryness. The residue was distilled to yield 4.7 g (87%) of product, b.p. (1.2 mm Hg) 115°-120° C.

Step C: Preparation of 5-(2-methoxyethyl)-2-sulfamoyl-benzo[b]thiophene

Employing the procedure substantially as described in Example 1, Step C but substituting for the 6-methoxybenzo[b]thiophene used therein, an equimolar amount of 5-(2-methoxyethyl)benzo[b]thiophene, there was produced the subject compound (66% yield) with m.p. 104°-108° C.

EXAMPLE 33

5-(2-Benzyloxyethyl)-2-sulfamoylbenzo[b]thiophene

Step A: Preparation of 5-(2-Benzyloxyethyl)benzo[b]thiophene

To a solution of NaH (60% oil dispersion, 2.4 g, 0.06 mol) in DMF (50 ml) heated at 60° C. with stirring under $N_2$ was added dropwise a solution of 5-(2-hydroxyethyl)benzo[b]thiophene (8.9 g, 0.05 mol) in DMF (50 ml). After ½ hour, a solution of benzyl bromide (10.3 g, 7.2 ml, d=1.438, 0.06 mol) in DMF (50 ml) was added dropwise. After 15 hours, the solution was poured into H₂O and the aqueous phase extracted with ethyl acetate (3×). The organic layers were backwashed with H₂O saturated NaCl, dried, filtered and concentrated to dryness. The residue was chromatographed on silica gel and the product was eluted with 10% (V/V) ethyl acetate-hexane to yield 9.7 g (72%) of product. The material was used directly in the next step without further purification.

Step B: Preparation of 5-(2-benzyloxyethyl)-2-sulfamoylbenzo[b]thiophene

Employing the procedure of Example 1, Step C but using the benzyl ether of Step A of this Example 33 as starting material, the product, m.p. 136°–138° C. was produced in 51% yield.

EXAMPLE 34

5-(2-Bromoethyl)-2-sulfamoylbenzo[b]thiophene

To a solution of 5-(2-methoxyethyl)-2-sulfamoylbenzo[b]thiophene (8.3 g, 0.031 mol) in 550 ml of methylene chloride at −78° C. was added dropwise under nitrogen, 100 ml of a solution of boron tribromide (BBr₃) (1M in hexane, 0.1 mol). The reaction was stirred at room temperature overnight (15 hours) following the addition. The mixture was cooled and diluted with 100 ml of cold water. The aqueous phase was separated and extracted 2× with methylene chloride. The original organic phase and the extracts were combined, dried, filtered and concentrated to dryness to yield 8.3 g (86%) of product with m.p. 118°–120° C.

EXAMPLE 35

5-(2-Acetoxyethyl)-2-sulfamoylbenzo[b]thiophene and 5-ethenyl-2-sulfamoylbenzo[b]thiophene A solution of 4.0 g (0.012 mol) of 5-(2-bromoethyl)-2-sulfamoylbenzo[b]thiophene, 2.0 g (0.024 mol) of sodium acetate and 40 ml of DMF was heated at 100° C. under nitrogen. After 15 hours the mixture was poured into water and the aqueous phase was extracted 3× with ethyl acetate. The extracts were dried, filtered and concentrated to dryness. The residue was chromatographed on silica gel by elution with 20% (V/V) ethyl acetate-hexane to yield 2.9 g (30%) of 5-ethenyl-2-sulfamoylbenzo[b]thiophene, m.p. 168°–170° C. (1,2-dichloroethane). Further elution with 40% (V/V) ethyl acetate-hexane yielded 3.74 g (59%) of 5-(2-acetoxyethyl)-2-sulfamoylbenzo[b]thiophene, m.p. 120°–122° C. (1,2-dichloroethane).

EXAMPLE 36

5-(2-Hydroxyethyl-2-sulfamoylbenzo[b]thiophene

A solution of 5-(2-acetoxyethyl)-2-sulfamoyl benzo[b]thiophene, (1.8 g, 0.006 mol), ethanol (50 ml) and 10% NaOH (50 ml) was heated at reflux. After 4.5 h, the mixture was poured into 3N HCl (50 ml) and extracted with ethyl acetate (3×). The organic extracts were washed with saturated Na₂CO₃, dried, filtered and concentrated to dryness to yield 1.5 g (97%) of product, m.p. 162°–164° C.

EXAMPLE 37

6-(2-Methyldioxolan-2-yl)-2-sulfamoylbenzo[b]thiophene

Step A: Preparation of 6-acetylbenzo[b]thiophene

6-Acetyl-2,3-dibromobenzo[b]thiophene (6.68 g, 20 mmole) was dissolved in a mixture of ethanol and ethyl acetate (100 ml each) and MgO (1.6 g) and (20% Pd(OH)₂)/C (800 mg) were added under a N₂ atmosphere. Hydrogenolysis was carried out at 40 psi of H₂ at room temperature for 3 hours. The catalyst was removed by filtration and the solvent was removed in vacuo. The residue was partitioned between CHCl₃ (100 ml) and H₂O (50 ml). The CHCl₃ layer was washed with H₂O (50 ml). The aqueous layers were combined and back-extracted with CHCl₃ (30 ml). The CHCl₃ solutions were combined, dried over Na₂SO₄ and the solvent evaporated in vacuo to yield 3.8 g of product which was used in the next step without further purification.

Step B: Preparation of 6-(2-methyldioxolan-2-yl)benzo[b]thiophene

A mixture of 6-acetyl benzo[b]thiophene (10.57 g, 60 mmole), p-toluenesulfonic acid (1.65 g) and ethylene glycol (33 ml) was heated to reflux in toluene (250 ml) for 2 hours with the continuous removal of H₂O using a Dean-Stark trap. The reaction mixture was allowed to cool to room temperature. Then extracted with 20% saturated NaHCO₃ (150 ml) and H₂O (2×150 ml). After drying over Na₂SO₄, the solvent was evaporated in vacuo and the residue was crystallized from hexanes (50 ml) yielding 9.66 g (73%) of product.

Step C: Preparation of 6-(2-methyldioxolan-2-yl)2-sulfamoylbenzo[b]thiophene

The title compound was prepared by the procedure used for the synthesis of 6-methoxy-2-sulfamoylbenzo[b]thiophene in Example 1, Step C.

After crystallization from ethyl acetate-hexanes 6.35 g (42%) of product was obtained, m.p. 127°–128° C.

EXAMPLE 38

6-Acetyl-2-sulfamoylbenzo[b]thiophene

The ketal product from Example 37 (4.4 g, 14.7 mmole) and p-toluenesulfonic acid (400 mg) were dissolved in acetone (90 ml). The mixture was stirred overnight. The solvent was removed in vacuo and the residue partitioned between ethyl acetate (200 ml) and 10% saturated NaHCO₃ solution (b 100 ml). The organic layer was washed with H₂O (2×100 ml) and dried over Na₂SO₄. The solvent was removed in vacuo and the residue was triturated with hot CHCl₃ (100 ml). Upon cooling, 3.4 g (90.6%) of product was obtained, m.p. 154°–155° C.

EXAMPLE 39

6-(1-Hydroxyethyl)-2-sulfamoylbenzo[b]thiophene

The acetyl compound from Example 38 (1.79 g, 7 mmole) was dissolved in 40 ml of CH₃OH, cooled to 0° C. and NaBH₄ (264 mg, 7 mmole) in 4 ml of 40% NaOH was added. The reaction mixture was stirred for 25 minutes then 2.5 g of NH₄Cl was added followed by 1 ml glacial acetic acid. The solvent was removed in vacuo and the residue partitioned between ethyl acetate (75 ml) and 20% saturated NaHCO₃ (50 ml). The ethyl acetate layer was washed with H₂O (50 ml) and the combined aqueous solution was back-extracted with ethyl acetate. The ethyl acetate extracts were combined and dried over Na₂SO₄. The solvent was removed in vacuo and the residue was crystallized from CHCl₃-dichloroethane yielding 1.56 g (86.7%) of product, m.p. 134°–35° C.

EXAMPLE 40

4-Chloro-5-hydroxy-2-sulfamoylbenzo[b]thiophene

A stirred solution of 5-hydroxy-2-sulfamoylbenzo[b]thiophene (3.0 g, 0.013 mole) in $CH_3CN$ (60 ml) was treated with N,N-dimethylformamide dimethylacetal (1.75 ml, 0.013 mole). Within 5 minutes, the protected sulfonamide started to precipitate. After 10 minutes, this was redissolved by the addition of $CH_3CN$ (65 ml). N-Chlorosuccinimide, (1.91 g, 0.0143 mole) was added in one portion and the mixture was stirred at ambient temperature. After 2 days, another 175 mg of N-chlorosuccinimide was added and stirring was continued for another 3 days. The solvent was evaporated under reduced pressure and the residual solid was triturated with $H_2O$ (100 ml) and collected. This solid then was suspended in 6N HCl (70 ml) and heated on the steam bath for 6½ hours. The resulting solid was extracted into ethyl acetate. Evaporation of the washed and dried extract under reduced pressure left 3.1 g (90%) of 4-chloro-5-hydroxy-2-sulfamoylbenzo[b]thiophene, m.p. 198°–201° C. Recrystallization from $H_2O$, decolorizing with charcoal, gave 2.6 g, m.p. 203°–205° C.

EXAMPLE 41

6-Hydroxy-2-sulfamoylbenzo[b]thiophene-6-sodium sulfate

A mixture of 3.00 g of 6-hydroxy-2-sulfamoylbenzo[b]thiophene and 3.00 g of sulfamic acid in 20 ml of dry pyridine were refluxed gently for 36 hours. At the end of the reaction, the pyridine was distilled from the mixture under vacuum at 50° C. The residue was dissolved in water and made basic by addition of concentrated ammonia. The solvent was evaporated. The product was separated from residual ammonium sulfamate by extraction into ethanol. The ethanol extract was filtered an evaporated to give 3.2 g of crude sulfate as the ammonium salt. The salt was dissolved in distilled water and titrated with 1 equivalent of sodium hydroxide. The solvent was evaporated leaving the crude sodium sulfate salt. A 2.64 g portion of the product was boiled with 40 ml of saturated sodium chloride solution and sufficient water was added to obtain a clear solution. Upon cooling, 2.00 g of a white solid separated. Elemental analysis showed the material to be a mixture of the desired product and 11.7% (by weight) sodium chloride.

Calculated for $C_8H_6NNaO_6S_3.0.117$ NaCl: C, 25.60; N, 3.73; H, 1.61; Cl, 7.12. Found: C, 25.87; N, 3.97; H, 1.54; Cl. 7.12.

Treating the ammonium salt produced in Example 41 with potassium chloride, tetramethylammonium chloride, pyridine, imidazole, pralidoxime chloride or thiamine in place of the sodium chloride used in Example 41 there are prepared the corresponding salts.

EXAMPLE 42

6-Hydroxy-2-sulfamoylbenzo[b]thiophene-6-disodium phosphate

A solution of 2.5 g of 6-hydroxy-2-sulfamoylbenzo[b]thiophene in 10 ml of pyridine was added over a 1 minute period to a well-stirred solution of 1.02 ml of phosphorous oxychloride in pyridine (10 ml) at 0° C. After 15 to 30 minutes the reaction mixture was poured into ice-water and the resulting solution was stirred for 15 minutes. The solvents were evaporated under high vacuum on a rotary evaporator. The product was resuspended in water and the pH of the solution was adjusted to 7.8±0.6. The solvents were removed and the solid dried under high vacuum. The solid was redissolved in 100 ml of distilled water. Gradual addition of 400 ml of acetone lead to precipitation of the title compound (1.50 g) as a monohydrate. Elemental analysis:

Calc'd for $C_8N_6NNa_2O_6PS_2.H_2O$: N, 3.77; C, 25:88; H, 2.17; S, 17.27. Found: N, 3.85; C, 25.64; H, 2.09; S, 17.32.

Other salts of the phosphate group are obtained by using the appropriate hydroxide in place of sodium hydroxide in the procedure above, such as potassium hydroxide, tetramethylammonium hydroxide, pyridine, imidazole, pralidoxime hydroxide and thiamine.

Mixed esters of the type:

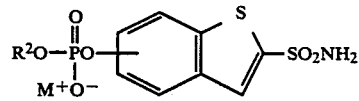

wherein $R^2$ is $C_{1-3}$alkyl or phenyl-$C_{1-3}$alkyl are prepared by reacting a hydroxy-2-sulfamoylbenzo[b]thiophene with an appropriate alkyldichlorophosphate; e.g. ethyldichlorophsophate, or benzyldichlorophosphate.

EXAMPLE 43

6-Hydroxy-5-methoxy-2-sulfamoylbenzo[b]thiophene

Step A: Preparation of 5-(4-Hydroxy-3-methoxybenzylidene)rhodanine

A mixture of vanillin (30.4 g, 0.2 mol), rhodanine (26.6 g, 0.2 mol), anhydrous sodium acetate (41 g, 0.5 mol) and glacial acetic acid was stirred and heated at reflux for one and one-half hours. The cooled reaction mixture was added to water (1200 mL) and the yellow-orange solid that separated was collected, washed with water and air dried; yield 46 g.

Step B: Preparation of 3-(4-Hydroxy-3-methoxyphenyl)-2-mercaptoacrylic acid The product from Step A was added to 20% sodium hydroxide solution (250 mL) and heated to 70°–75° C. with stirring for one hour. The resulting solution was chilled in an ice bath and added rapidly, with stirring, to cold 10% hydrochloric acid (350 mL). The yellow solid was collected, washed with water and dried at 50° C.; yield 36 g.

Step C: Preparation of 6-Hydroxy-5-methoxybenzo[b]thiophene-2-carboxylic acid Iodine (90 g) was added to a stirred mixture of the product from Step B (73 g) and 90% ethanol (2000 mL). The resultant dark mixture was heated at reflux for 24 hours. Saturated sodium bisulfite solution (20 mL) was added to the cooled reaction mixture and the ethanol was removed in vacuo. The aqueous residue was diluted to 1500 ml with water and extracted with ethyl acetate (4×400 mL). The combined extracts were evaporated in vacuo and the residue was heated on the steam bath with 1N sodium hydroxide solution (1500 mL) for 3 hours. The solution was treated with charcoal, filtered, diluted to 2500 mL with water and acidified with concentrated hydrochloric acid. The precipitated solid was collected, washed with water and dried; yield 36.8 g.

Step D: Preparation of 6-Hydroxy-5-methoxybenzo[b]thiophene

A mixture of the product from Step C (8 g), copper dust (2 g) and quinoline (40 mL) was heated under reflux for two hours. The hot reaction mixture was poured onto crushed ice (200 g), acidified with 6N hydrochloric acid and filtered. The filtrate was washed with saturated sodium chloride solution, dried ($Na_2SO_4$) and filtered and the solvent was evaporated in vacuo, leaving 5 g of waxy solid.

Step E: 6-Hydroxy-5-methoxy-2-sulfamoylbenzo[b]thiophene

To a cooled ($-20°$ C.) solution of 6-hydroxy-5-methoxybenzo[b]thiophene (15 g) in dry tetrahydrofuran (300 mL) was added butyl lithium (117 mL, 1.6N in hexane). After addition was complete, the reaction mixture was allowed to warm to 20° C. and $SO_2$ gas was introduced over the surface of the stirred mixture. Addition was continued until an aliquot dissolved in water no longer tested alkaline (pH paper). After stirring for one hour, ether (500 mL) was added and the greyish-green solid was collected on a filter. This solid was added to a solution of sodium acetate (13.8 g) in water (500 mL) followed by the addition of hydroxylamine-O-sulfonic acid (41.7 g). After 24 hours, the solid was collected, washed with chloroform and recrystallized from water, 4.9 g, m.p. 201°-204° C.

Anal. Calc'd for $C_9H_9NO_4S_2$: C, 41.69; H, 3.50; N, 5.40. Found: C, 42.50; H, 3.55; N, 5.38.

Employing the procedures described in Example 43, Steps A through E, but starting with 3-hydroxy-4-methoxybenzaldehyde, there is produced 5-hydroxy-6-methoxy-2-sulfamoylbenzo[b]thiophene.

EXAMPLE 44

5,6-Dihydroxy-2-sulfamoylbenzo[b]thiophene

A stirred mixture of 5-hydroxy-5-methoxysulfamoylbenzo[b]thiophene (4.9 g) and pyridine hydrochloride (15 g) was heated to 190°-200° C. for 1.5 hours. The warm reaction mixture was diluted with water (200 mL) and extracted with ethyl acetate (4×150 ml). The extracts were washed with water, saturated sodium chloride solution, dried ($Na_2SO_4$), filtered and evaporated under reduced pressure to give a tan solid residue of 1.8 g. Recrystallization from nitromethane gave material of m.p. 233°-235° C.

Anal. Calc'd for $C_8H_7NO_4S_2$: C, 39.16; H, 2.88; N, 5.71 Found: C, 38.85; H, 2.74; N, 5.77.

EXAMPLE 45

5-N,N-Dimethylcarbamoyloxy-2-sulfamoylbenzo[b]thiophene

A solution of 2.3 g (10 mmoles) of 5-hydroxy-2-sulfamoylbenzo[b]thiophene in 50 ml of pyridine was treated with 200 mg of 4-dimethylaminopyridine and finally 2.5 ml (2.9 g, 27 mmoles) of dimethylcarbamyl chloride. The resultant clear solution was stirred at room temperature for 48 hours, when it was poured into a mixture of 200 g of chopped ice and 100 ml of concentrated HCl. The precipitated solid was collected and washed with cold $H_2O$ until the washings were neutral. Drying gave 2.25 g (75%) of tan powder which was crystallized from isopropyl alchol to give 1.6 g of product, m.p. 192°-194° C.

EXAMPLE 46

5-(Carboxymethoxy)-2-sulfamoylbenzo[b]thiophene

A suspension of 50% sodium hydride (0.32 g, 0.0066 m) in dry dimethylformamide (15 ml) was stirred at 25° C. under nitrogen while N,N-dimethyl-N'-(5-hydroxybenzo[b]thiophene-2-sulfonyl)amidine (1.50 g, 0.0053 m) was added portionwise over 15 minutes. The mixture was stirred at 70° C. for 15 minutes, then ethyl bromoacetate (1.10 g, 0.0066 m) was added rapidly and the mixture was heated at 70° C. for 16.5 hours. The reaction was added to water (150 ml) and extracted with ethyl acetate (3×100 ml). The extracts were washed with $H_2O$, dried over $Na_2SO_4$ and concentrated under reduced pressure. The residue was stirred at 40° C. for 4 hours in a mixture of 2N NaOH (14 ml) and methanol (7 ml). After evaporating the solvent under reduced pressure, the residue was dissolved in water (35 ml), acidified with 3N HCl and the solid was collected to yield 0.95 g (63%) of product melting at 200°-203° C. An analytical sample melted at 202.5°-204° C. after recrystallization from nitromethane.

EXAMPLE 47

5-(Carbamoylmethoxy)-2-sulfamoylbenzo[b]thiophene

A mixture of 5-(carboxymethoxy)-2-sulfamoylbenzo[b]thiophene (5.00 g, 0.017 m) in thionyl chloride (50 ml) was refluxed for one hour and then concentrated under reduced pressure. The residue was treated with cold concentrated ammonium hydroxide solution (75 ml) and stirred at 25° C. for one hour. The solution was concentrated under reduced pressure for a few minutes until a solid began to precipitate. The solid was collected to afford 3.34 g (69%) of product melting at 197°-198° C. An analytical sample melted on 200°-201° C. on recrystallization from 95% ethanol.

EXAMPLE 48

5-(2-Aminoethoxy)-2-sulfamoylbenzo[b]thiophene Hydrochloride

A suspension of 5-(carbamoylmethoxy)-2-sulfamoylbenzo[b]thiophene (0.50 g, 0.0017 mole) in dry tetrahydrofuran was stirred and heated to reflux in an oil bath at 80° C. under nitrogen while 10.0M borane-dimethylsulfide complex (0.4 ml, 0.0040 m) was added over 20 minutes, allowing dimethylsulfide to distill from the reaction mixture using a Claisen distillation head. An additional 5 ml of tetrahydrofuran and 0.2 ml of 10.0M borane-dimethylsulfide complex was added and the mixture was refluxed for one hour. After cooling to room temperature, methanol (3 ml) was added dropwise to decompose excess borane-dimethylsulfide complex and then 5 ml of ether saturated with hydrogen chloride was added and the mixture was stirred at 25° C. for approximately 16 hours. The product was collected to give 0.37 g (71%) of material melting at 222°-224° C. An analytical sample melted at 234°-236° C. after recrystallization from methanol-ether.

EXAMPLE 49

6-Amino-2-sulfamoylbenzo[b]thiophene

Step A: Preparation of 6-Acetamido-2-sulfamoylbenzo[b]thiophene

A solution of 6-acetylbenzo[b]thiophene-2-sulfonamide (5.1 g, 0.02 mole) in glacial acetic acid (50 ml) and concentrated $H_2SO_4$ (20 ml) was stirred and heated to 65° C. Sodium azide (5.0 g, 0.077 mole) was added in portions over a 1 hour period. After heating the mixture at 80° C. for another 3 hours, it was poured into a stirred, saturated NaOAc solution (500 ml) cooled in an ice bath. The resulting mixture was refrigerated overnight. The solid was collected, resuspended in water (300 ml), and recollected to obtain 5.25 g (97%) of crude product, m.p. 214°–217° C. Recrystallizations from $CH_3OH$ with charcoal decolorization and from $CH_3CN$ afforded 1.5 g of 6-acetamido-2-sulfamoylbenzo[b]thiophene, m.p. 231°–232.5° C.

Step B: Preparation of 6-Amino-2-sulfamoylbenzo[b]thiophene

6-Acetamido-2-sulfamoylbenzo[b]thiophene (0.8 g, 3 mmole) was suspended in 1N HCl (24 ml). The stirred mixture was heated to refluxing for 1 hour when a clear solution was obtained. After dilution with water (25 ml), the cooled solution was neutralized with saturated $NaHCO_3$ solution. The product precipitated and was collected to obtain 0.57 g (83%), m.p. 240°–241° C. dec. This material was combined with 1.3 g of comparable crude product from two other runs and recrystallized from $CH_3CN$, decolorizing with charcoal, to yield 1.46 g of 6-amino-2-sulfamoylbenzo[b]thiophene, m.p. 239°–240° C. (dec).

EXAMPLE 50

5-(2-Aminoethyl)-2-sulfamoylbenzo[b]thiophene

Step A: Preparation of 5-(2-Azidoethyl)-2-sulfamoylbenzo[b]thiophene

Under nitrogen, a solution of 5-(2-bromoethyl)-2-sulfamoylbenzo[b]thiophene (1.2 g, 0.0037 mol), $NaN_3$ (0.6 g, 0.0092 mol) and DMF (25 ml) was heated at 100° C. After 18 hours, the solution was cooled, poured into $H_2O$, and filtered to yield 0.8 g of product. The filtrate was extracted with ethyl acetate (2x). The organic layers were dried, filtered and concentrated to dryness to yield an additional 0.4 g of product (75%).

Step B: Preparation of 5-(2-aminoethyl)-2-sulfamoylbenzo[b]thiophene

A solution of product from Step A (1.2 g, 0.004 mol), ethanol (125 ml), $CHCl_3$ (2.2 ml), and 10% Pd on C (0.45 g) was hydrogenated on a Parr shaker at 55 psi. After overnight shaking, the contents were filtered under a blanket of $N_2$ through a filter aid pad. The solution was concentrated to dryness and the residue crystallized from $CH_3OHCH_3CN$ to yield 0.62 g of product; m.p. 295°–297° C.

EXAMPLE 51

5-(Trifluoromethylimidazol-2-yl)-2-sulfamoylbenzo[b]thiophene

Step A: Preparation of 5-Formylbenzo[b]thiophene

Under $N_2$, NBS (6 g, 0.034 mol) was added to a solution of 5-methylbenzo[b]thiophene (30.8 g, 0.21 mol), benzoylperoxide (1.6 g) in $CCl_4$ (300 ml) and was heated at reflux. After 15 minutes, the remainder of the NBS (35 g, 0.2 mol) was added over a period of 5 minutes and heated at reflux for 1.5 hours. The reaction mixture was then cooled, filtered and the filtrate washed with $H_2O$ (2x), dried, filtered and concentrated to dryness. The residue was dissolved in $CHCl_3$ (130 ml) and added to a solution of hexamethylenetetramine (33.6 g, 0.24 mol) in $CHCl_3$ (60 ml). After 0.5 hour, the reaction mixture was cooled, filtered and the solid washed with hexane. After drying, the solid was dissolved in acetic acid-$H_2O$ (275 ml) and heated at reflux for 2 hours. The concentrated HCl (55 ml) was added and the mixture refluxed an additional 5 minutes. After cooling, the solution was extracted with ether (3x), and the organic extracts were backwashed with saturated $Na_2CO_3$ (2x), dried, filtered, and concentrated to dryness to yield 16.4 g (48%) of product.

Step B: Preparation of 5-(1,3-Dioxolan-2-yl)benzo[b]thiophene

A solution of product from Step A (16.4 g, 0.1 mol), toluene (300 ml), p-toluenesulfonic acid (1.0 g) and ethylene glycol (20 ml) was heated at reflux with the aid of a Dean-Stark trap. After 6 hours, the organic layer was cooled, washed with saturated $Na_2CO_3$. The $Na_2CO_3$ layer was extracted with ethyl acetate (2x). The combined organic extracts were dried, filtered and concentrated to dryness. The residue was distilled at 149°–153° C. at 0.3 mm Hg to yield 16.4 g (79%) of product.

Step C: Preparation of 5-Formyl-2-sulfamoylbenzo[b]thiophene

Under $N_2$, a solution of product from Step B (6.2 g, 0.03 mol) in dry THF (75 ml) was cooled to less than −40° C. and then n-butyl lithium (20 ml, 1.6M in hexane, 0.032 mol) was added dropwise maintaining the temperature below −40° C. After stirring for an additional 0.5 hour at about −40° C. $SO_2$ gas was introduced over the surface of the reaction for 20 minutes. Then, ether was added to the suspension and allowed to stir at ambient temperature over 1 hour. The solid was removed by filtration and dried. The solid was suspended in $CH_2Cl_2$ (150 ml) and the mixture cooled in an ice bath while adding N-chlorosuccinimide (4.0 g, 0.03 mol). After complete addition, the suspension was stirred at room temperature for 18 hours, when the suspension was filtered and concentrated to dryness. The residue was treated with acetone (50 ml) and aqueous $NH_3$ (50 ml), and the solution concentrated to remove the acetone. The resulting suspension was filtered and the resulting solid (5 g) was dissolved in acetone (90 ml) and 1N HCl (90 ml) and heated on a steam bath for 15 minutes. The mixture was poured into $H_2O$ and extracted with ethyl acetate (3x). The organic layers were dried, filtered and concentrated to dryness to yield 3.3 g (48%) of product.

Step D: Preparation of 5-(4-trifluoromethylimidazol-2-yl)-2-sulfamoylbenzo[b]thiophene A solution of

(1.35 g, 0.005 mol), sodium acetate trihydrate (0.01 mol) in H$_2$O (10 ml) was heated on a steam bath for 15 minutes and then added in one portion to a solution of the product from Step C (1.1 g, 0.005 mol) in CH$_3$OH (40 ml) and concentrated aqueous NH$_3$ (10 ml). After stirring overnight at room temperature, an additional amount of

(1 g) was added. After 5 hours, the solvents were removed under reduced pressure and the residue chromatographed on silica gel eluting gradiently with 2% CH$_3$OH—CHCl$_3$ to 100% CH$_3$OH. The crude product was crystallized from CH$_3$CN to yield 0.85 g (50%) of product; m.p. 285°–286° C.

EXAMPLE 52

5-[2-(Dimethylamino)ethylthiomethyl]-2-sulfamoylbenzo[b]thiophene

To a stirred solution of 2-dimethylaminoethanethiol hydrochloride (14.17 g, 0.10 mol) in 125 ml of dry DMF was added portionwise 60% sodium hydride in mineral oil (8.0 g, 0.2 mol) under a nitrogen atmosphere over ½ hour with warming on the steam bath. The mixture was stirred an additional ½ hour and then cooled in ice. To the cold suspension was added dropwise a solution of 5-bromomethyl-2-sulfamoylbenzo[b]thiophene (7.66 g, 0.025 mol) in 25 ml of DMF. The mixture was stirred for an additional 1 hour at ice bath temperature. The mixture was filtered and the filtrate was concentrated in vacuo at 0.5 mm at room temperature. The solid residue was combined with the filtered solid and was dissolved in 3N HCl (100 ml). The acid solution was extracted with CHCl$_3$ (3×50 ml), neutralized with NaHCO$_3$ and concentrated to dryness in vacuo. The residual solid was extracted with CHCl$_3$ (3×100 ml). The CHCl$_3$ extracts were dried over anhydrous Na$_2$SO$_4$, filtered and concentrated in vacuo at room temperature. The solid obtained contained some polar impurity which was removed by trituration with hot water. There was recovered 2.8 g of product (Yield 34%); m.p. 132–133%.

EXAMPLE 53

5-[2-(Dimethylamino)ethylsulfinylmethyl]-2-sulfamoylbenzo[b]thiophene

To a partial solution of 5-[2-(dimethylamino)ethylthiomethyl]-2-sulfamoylbenzo[b]thiophene (1.32 g, 0.004 mol) in 20 ml of ethanol and 40 ml of water was added sodium metaperiodate (0.94 g, 0.0044 mol) and the mixture was stirred at room temperature for 16 hours overnight. The reaction mixture was filtered and the filtrate was evaporated to dryness in vacuo. The white solid residue was recrystallized twice from 4/1 (V/V) water/ethanol and chromatographed on silica gel eluting with 7.5% (V/V) methanol/CHCl$_3$. There was recovered 0.88 g of white solid, m.p. 180°–183° C., dec. (Yield 64%).

EXAMPLE 54

5-[2-(Dimethylamino)ethylsulfonylmethyl]-2-sulfamoylbenzo[b]thiophene

To a solution of 5-[2-(dimethylamino)ethylthiomethyl]-2-sulfamoylbenzo[b]thiophene (2.34 g, 0.0064 mol) in 20 ml of water at 40°–45° C. was added potassium peroxymonosulfate, "oxone", (5.93 g, 0.0096 mol). The mixture was stirred at room temperature over night and heated on the steam bath for 2½ hours. The mixture was cooled and basified with NaHCO$_3$. Filtration gave 2.5 g of crude product. Purification by silica gel chromatography eluting with 10% (V/V) methanol/CHCl$_3$ gave 0.78 g of pale pink solid, m.p. 185.5°–187° C., dec. (Yield 34%).

EXAMPLE 55

5-(Carboethoxymethoxy)-2-sulfamoylbenzo[b]thiophene

A mixture of 5-(carboxymethoxy)benzo[b]thiophene-2-sulfonamide (1.50 g, 0.0052 m) in ethanol (15 ml) and concentrated sulfuric acid (3 ml) was refluxed with stirring for 5 hours. Ethanol was evaporated under reduced pressure, the residue was treated with H$_2$O (25 ml) and extracted with ethyl acetate (50 ml and 2×25 ml). The combined extracts were washed with H$_2$O, saturated sodium bicarbonate solution (2×25 ml), and three times with H$_2$O. After drying over Na$_2$SO$_4$, the solvent was evaporated under reduced pressure to afford 1.43 g (87%) of product. Recrystallization from nitromethane afforded 1.12 g of analytically pure product melting at 167.5°–168° C.

EXAMPLE 56

5-(N-Hydroxycarbamoylmethoxy)-2-sulfamoylbenzo[b]thiophene

A warm solution of potassium hydroxide (2.58 g, 0.046 m) in methanol (7 ml) was added to a warm solution of hydroxylamine hydrochloride (1.60 g, 0.023 ml) in methanol (10 ml) under nitrogen. After cooling in an ice bath for 10 minutes, the solid was filtered and washed with methanol. The combined filtrate and washings were added to a warm solution of 5-(carboethoxymethyl-2-sulfamoylbenzo[b]thiophene (3.57 g, 0.011 ml) in methanol (170 ml) and the mixture was stirred at ambient temperature for 49 hours. The solid was collected, washed with ether, and then heated to reflux in 1.5N acetic acid (17 ml) until a clear solution resulted. After cooling to ambient temperature, the product was collected to yield 2.16 g (65%) of crude product melting at 138° C. Preparative TLC afforded 0.67 g of pure product melting at 153° C. An analytical sample melted at 156° C. after recrystallization from nitromethane.

For use in treatment of conditions relieved by the inhibition of carbonic anhydrase, the active compound can be administered either systemically, or, in the treatment of the eye, topically. The dose administered can be from as little as 0.1 to 25 mg or more per day, singly, or preferably on a 2 to 4 dose per day regimen although a single dose per day is satisfactory.

When administered for the treatment of elevated intraocular pressure or glaucoma, the active compound is most desirably administered topically to the eye, although systemic treatment is, as indicated, also possible.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation. In such formulations, from 0.1% to 15% by weight can be employed. The objective is to administer a dose of from 0.1 to 10 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

The following examples of ophthalmic formulations are given by way of illustration.

EXAMPLE 57

| | | |
|---|---|---|
| 6-(2-Sulfamoylbenzo[b]thienyl) 2,2-dimethyl propionate (I) | 1 mg. | 15 mg. |
| Monobasic sodium phosphate .2H$_2$O | 9.38 mg. | 6.10 mg. |
| Dibasic sodium phosphate .12H$_2$O | 28.48 mg. | 16.80 mg. |
| Benzalkonium chloride | 0.10 mg. | 0.10 mg. |
| Water for injection q.s. ad. | 1.0 ml. | 1.0 ml. |

Compound I, phosphate buffer salts, and benzalkonium chloride are added to and dissolved in water. The pH of the composition is adjusted to 6.8 and diluted to volume. The composition is rendered sterile by ionizing radiation.

EXAMPLE 58

| | |
|---|---|
| 6-(2-Sulfamoylbenzo[b]thienyl) 2-methylpropionate (II) | 5 mg. |
| petrolatum q.s. ad. | 1 gram |

Compound II and the petroleum are aseptically combined.

EXAMPLE 59

| | |
|---|---|
| 6-(2-Sulfamoylbenzo[b]thienyl) 2-methylpropionate | 1 mg. |
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ¼ hour.

EXAMPLE 60

| | |
|---|---|
| 6-(2-Sulfamoylbenzo[b]thienyl) acetate | 1 mg. |
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R.H. cabinet until it is pliable. Appropriately sized inserts are cut from the film.

EXAMPLE 61

| | |
|---|---|
| 6-(2-Sulfamoylbenzo[b]thienyl) acetate | 1 mg. |
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R.H. cabinet until it is pliable. Appropriately sized inserts are then cut from the film.

EXAMPLE 62

| | |
|---|---|
| 6-(2-Sulfamoylbenzo[b]thienyl) acetate | 1 mg. |
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88%, R.H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

The following examples illustrate preparation of the improved ophthalmic suspension compositions of the present invention.

EXAMPLE 63

The following materials are admixed in a 1250 ml bottle: 24 g of 6-(2-sulfamoylbenzo[b]thienyl) 2,2-dimethylpropionate which is a sufficient amount of medicament to result in a concentration of 10 mg per ml in the final samples, allowing for previously established 3.0% average; 0.4 g sodium bisulfite, 12 g NaCl, and 28 ml water (at 180° F.). This mixture, (I), is autoclaved for 30 minutes at 121° C. under 15 psig. Separately, 3 g of hydroxyethylcellulose in 720 ml of water (II) and 0.4 g of lecithin in 80 ml of water (III) were autoclaved for 30 minutes at 121° C. Then, (III) is admixed with (I) for 2 hours, and the resultant mixture poured into (II). Another mixture (IV) is prepared from 20 g of sorbitol, 2.36 ml of benzalkonium chloride, 10 g of disodium edetate, and water to give a final solution volume of 900 ml. Then, (IV) is added to the mixture of (I), (II), and (III) in sufficient quantity to give 1.8 l. overall. The 1.8 l. mixture of I, II, III, and IV is then taken and homogenized using a homogenizer at 2000 psig. Stock solutions are then prepared for polyoxyethylene (20) sorbitan monooleate by dissolving 3 g of the material in 100 ml of water, and of benzyl alcohol/β-phenyl-ethyl alcohol by admixing 50 ml of each alcohol. Varying quantities of the two stock solutions are then added to four 90 ml aliquots of the homogenized mixture of (I), (II), (III), and (IV) prepared as described above, together with sufficient water to give a total of 100 ml for each of four different samples.

Other formulations, in an oil vehicle and an ointment are exemplified in the following examples.

EXAMPLE 64

Solution Composition

| | |
|---|---|
| 6-(2-Sulfamoylbenzo[b]thienyl) 2,2-dimethylpropionate | 0.1 mg. |
| Peanut oil q.s. ad. | 0.10 mg. |

The solution is rendered sterile by filtration through a sterilizing filter.

EXAMPLE 65

| | |
|---|---|
| 6-(2-Sulfamoylbenzo[b]thienyl) cyclopentaneacetate | 0.5 gm. |
| Petrolatum q.s. ad. | 1 gram |

The compound and the petrolatum are aseptically combined.

What is claimed is:

1. A compound of structural formula:

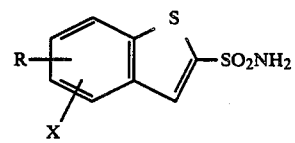

or an ophthalmologically or pharmaceutically acceptable salt thereof, wherein:

X is hydrogen, chloro, bromo or fluoro, $C_{1-3}$alkyl, hydroxy or $C_{1-3}$alkoxy; and R is:

wherein
$R^5$ and $R^6$ are independently:
(a) hydrogen,
(b) $C_{1-18}$ alkyl, either straight or branched chain,
(c) $C_{3-6}$ cycloalkyl,
(d) $C_{3-6}$ cycloalkyl-$C_{1-3}$ alkyl,
(e) aryl-$C_{1-3}$ alkyl wherein the aryl group is phenyl or naphthyl and is either unsubstituted or substituted with one or more of chloro, bromo, fluoro, $C_{1-3}$ alkyl or $C_{1-3}$ alkoxy,
(f)

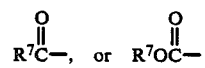

wherein R⁷ is
(i) $C_{1-18}$ alkyl, either straight or branched chain,
(ii) aryl as previously defined, either unsubstituted or substituted with one or more of chloro, bromo, fluoro, $C_{1-3}$ alkyl, or $C_{1-3}$ alkoxy,
(iii) aryl-$C_{1-3}$ alkyl wherein the aryl group is as previously defined and is either unsubstituted or substituted with one or more of chloro, bromo, fluoro, $C_{1-3}$ alkyl or $C_{1-3}$ alkoxy,
(iv) amino-$C_{1-18}$ alkyl either straight or branched chain; or
(g) $R^5$ and $R^6$ if lower alkyl, are joined together directly or through a heteroatom selected from O or N to form a 5 or 6-membered heterocycle selected from pyrrolidine, piperidine, morpholine, and piperazine.

2. The compound of claim 1, wherein R is in the 5 or 6 position.

3. The compound of claim 1, wherein X is hydrogen.

4. An ophthalmic composition for the topical treatment of glaucoma and elevated intraocular pressure comprising an ophthalmologically acceptable carrier and an effective intraocular pressure lowering amount of a compound with structural formula:

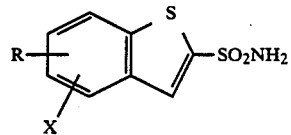

or an ophthalmologically acceptable salt thereof, wherein R and X are as defined in claim 1.

5. The composition of claim 4, wherein R is in the 5 or 6 position.

6. The composition of claim 5, wherein X is hydrogen.

7. A method of treating glaucoma and elevated intraocular pressure which comprises topical ocular application to a patient in need of such treatment of an effective intraocular pressure-lowering amount of a compond with structural formula:

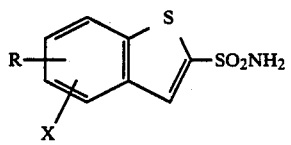

or an ophthalmologically acceptable salt thereof, wherein R and X are as defined in claim 1.

8. The method of claim 7, wherein R is in the 5 or 6 position.

9. The method of claim 8, wherein X is hydrogen.

* * * * *